(12) United States Patent
Koyrakh et al.

(10) Patent No.: US 10,561,371 B2
(45) Date of Patent: Feb. 18, 2020

(54) DYNAMIC ADAPTIVE RESPIRATION COMPENSATION WITH AUTOMATIC GAIN CONTROL

(71) Applicant: St. Jude Medical, Atrial Fibrillation Division, Inc., St. Paul, MN (US)

(72) Inventors: Lev A. Koyrakh, Plymouth, MN (US);
Eric J. Voth, Maplewood, MN (US);
John A. Hauck, Shoreview, MN (US);
Jeffrey A. Schweitzer, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1251 days.

(21) Appl. No.: 14/800,910

(22) Filed: Jul. 16, 2015

(65) Prior Publication Data
US 2015/0366512 A1    Dec. 24, 2015

Related U.S. Application Data

(62) Division of application No. 12/980,515, filed on Dec. 29, 2010, now Pat. No. 9,113,807.

(51) Int. Cl.
| | | |
|---|---|---|
| A61B 5/00 | (2006.01) | |
| A61B 5/06 | (2006.01) | |
| A61B 5/053 | (2006.01) | |

(52) U.S. Cl.
CPC ............ *A61B 5/7207* (2013.01); *A61B 5/053* (2013.01); *A61B 5/061* (2013.01); *A61B 5/063* (2013.01);
(Continued)

(58) Field of Classification Search
None
See application file for complete search history.

(56) References Cited

U.S. PATENT DOCUMENTS

| 5,662,108 A | 9/1997 | Budd |
| 5,697,377 A * | 12/1997 | Wittkampf ............. A61B 5/042 128/899 |

(Continued)

FOREIGN PATENT DOCUMENTS

| CN | 1901835 | 1/2007 |
| WO | 2010/023615 | 3/2010 |

OTHER PUBLICATIONS

Title: International Search Report and Written Opinion Citation: PCT/US2011/051447 Publication Date: Jan. 5, 2012.
(Continued)

*Primary Examiner* — Katherine L Fernandez
*Assistant Examiner* — Michael S Kellogg
(74) *Attorney, Agent, or Firm* — Dykema Gossett PLLC

(57) ABSTRACT

A system for determining a location of an electrode of a medical device (e.g., a catheter) in a body of a patient includes a localization block for producing an uncompensated electrode location, a motion compensation block for producing a compensation signal (i.e., for respiration, cardiac, etc.), and a mechanism for subtracting the compensation signal from the uncompensated electrode location. The result is a corrected electrode location substantially free of respiration and cardiac artifacts. The motion compensation block includes a dynamic adaptation feature which accounts for changes in a patient's respiration patterns as well as intentional movements of the medical device to different locations within the patient's body. The system further includes an automatic compensation gain control which suppresses compensation when certain conditions, such as noise or sudden patch impedance changes, are detected.

15 Claims, 14 Drawing Sheets

(52) U.S. Cl.
CPC ............ *A61B 5/6801* (2013.01); *A61B 5/721* (2013.01); *A61B 5/7267* (2013.01); *A61B 5/742* (2013.01); *A61B 5/0044* (2013.01); *A61B 5/0536* (2013.01); *A61B 5/0538* (2013.01); *A61B 5/06* (2013.01); *A61B 5/7203* (2013.01)

(56) References Cited

U.S. PATENT DOCUMENTS

| | | | |
|---|---|---|---|
| 5,983,126 | A | 11/1999 | Wittkampf |
| 6,233,476 | B1 | 5/2001 | Strommer |
| 6,282,440 | B1* | 8/2001 | Brodnick ............ A61B 5/04011 600/512 |
| 6,859,550 | B2 | 2/2005 | Oh |
| 7,263,397 | B2 | 8/2007 | Hauck |
| 7,684,850 | B2 | 3/2010 | Govari |
| 7,848,787 | B2* | 12/2010 | Osadchy ................ A61B 5/053 128/899 |
| 2004/0254437 | A1* | 12/2004 | Hauck .................. A61B 5/0422 600/374 |
| 2005/0165457 | A1 | 7/2005 | Benser |
| 2006/0173251 | A1 | 8/2006 | Govari et al. |
| 2006/0241401 | A1 | 10/2006 | Govari et al. |
| 2007/0028220 | A1* | 2/2007 | Miller ................ G05B 23/0278 717/124 |
| 2007/0038078 | A1 | 2/2007 | Osadchy |
| 2007/0060833 | A1 | 3/2007 | Hauck |
| 2008/0033282 | A1 | 2/2008 | Bar-Tal |
| 2008/0221459 | A1 | 9/2008 | Craven |
| 2008/0228060 | A1 | 9/2008 | Tegg |
| 2009/0088632 | A1 | 4/2009 | Khamene et al. |
| 2009/0092181 | A1 | 4/2009 | Sontowski |
| 2009/0192366 | A1 | 7/2009 | Mensinger |
| 2009/0275827 | A1* | 11/2009 | Aiken .................... A61B 5/053 600/424 |
| 2009/0318995 | A1* | 12/2009 | Keel ........................ A61B 5/11 607/17 |
| 2010/0079158 | A1 | 4/2010 | Bar-Tal et al. |

OTHER PUBLICATIONS

Golub, G. H., "Singular Value Decomposition and Least Squares Solutions", Handbook Series Linear Algebra: Singular Value Decomposition and Least Squares Solutions' by G. H. Golub and C. Reinsch published Numer. Math. vol. 14, Issue 5, 403-420 (t970), Apr. 1970.

Johnson, Richard M., "On a theorem stated by Eckart and Young", Psychometrika, vol. 28, No. 3, pp. 259-263, Sep. 1963.

Author: Moore-Penrose, Title: Moore-Penrose pseudinverse of matrix Citation: Moore-Penrose pseudinverse of matrix—MATLAB, mathworks company, published online, access date Nov. 29, 2012.

Shlens, Jonathon, "A tutorial on principle component analysis", Center for Neural Science, New York University, Systems Neurobiology Laboratory, Salk Institute for Biiological Studies, Apr. 22, 2009.

Supplementary European Search Report in EP Application No. 11852736.5 (dated Mar. 6, 2015).

* cited by examiner

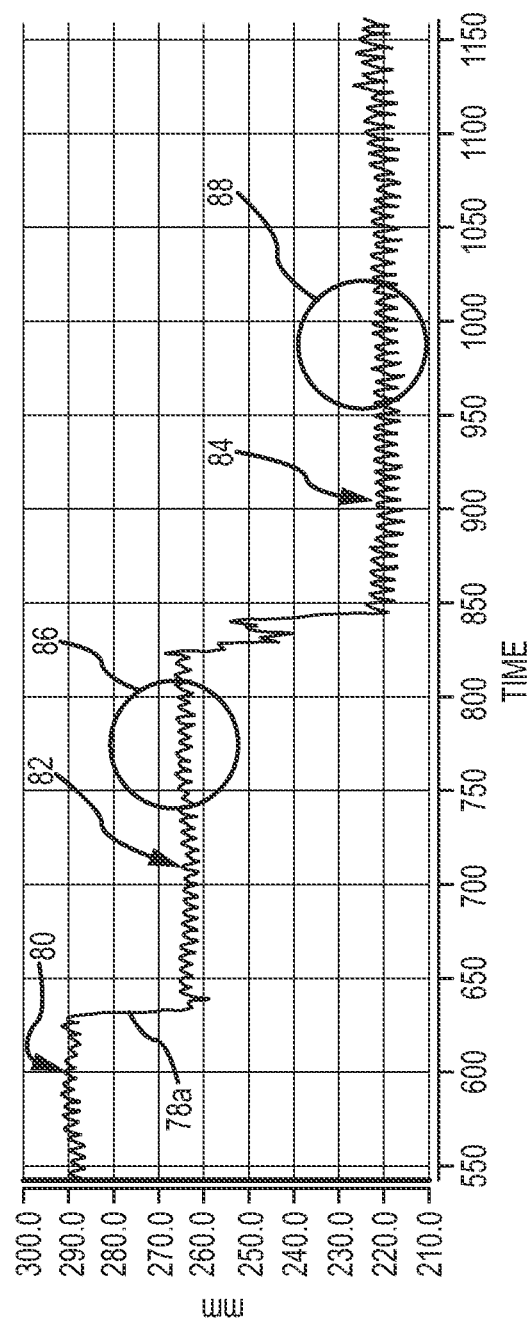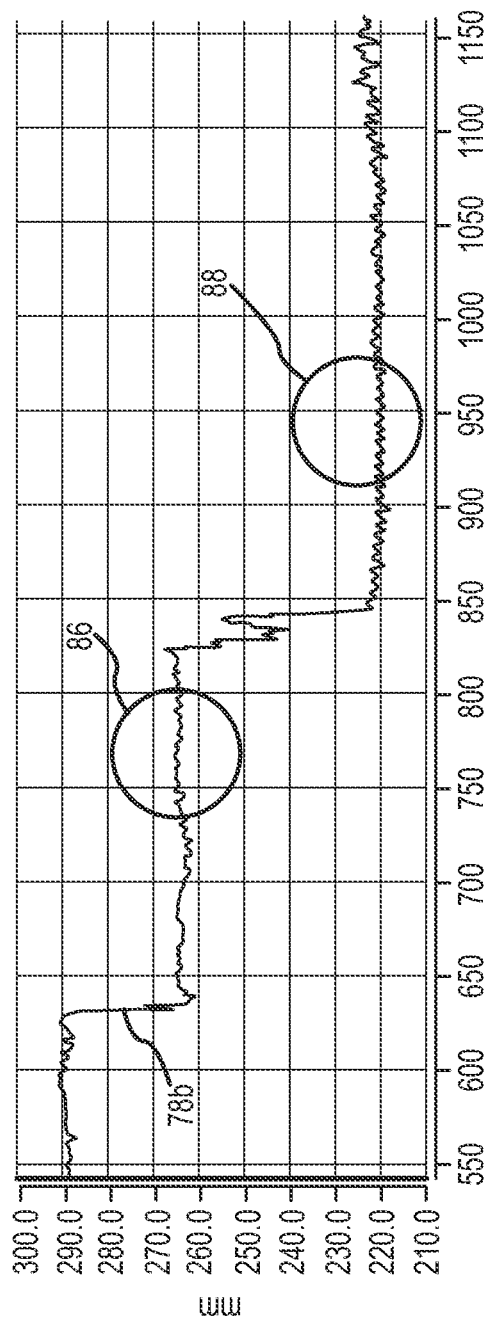

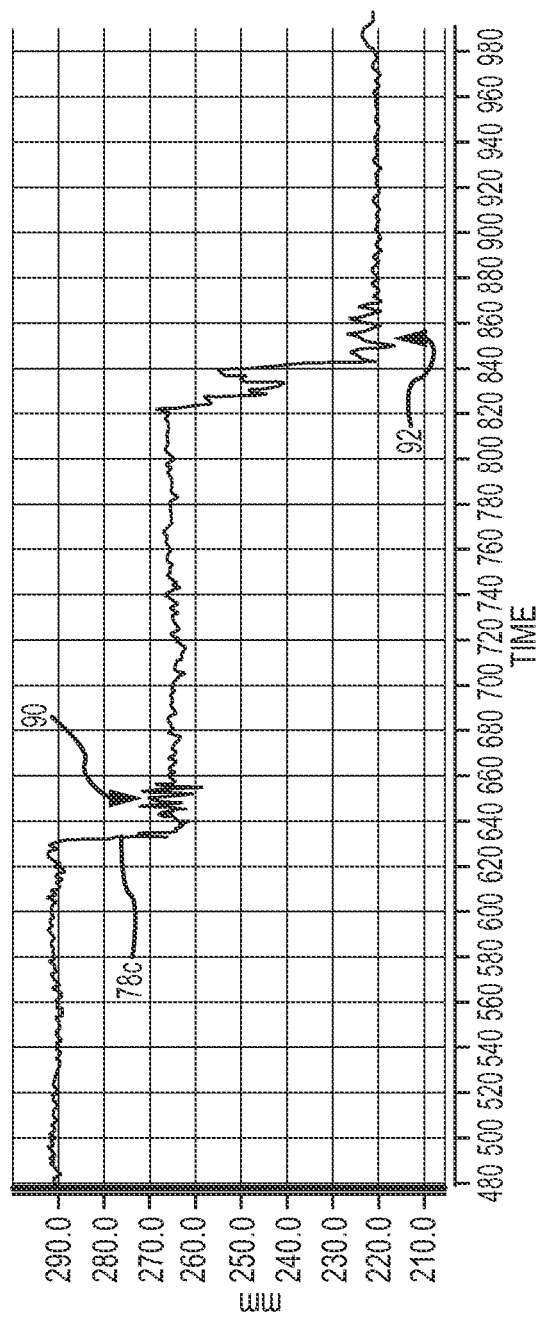
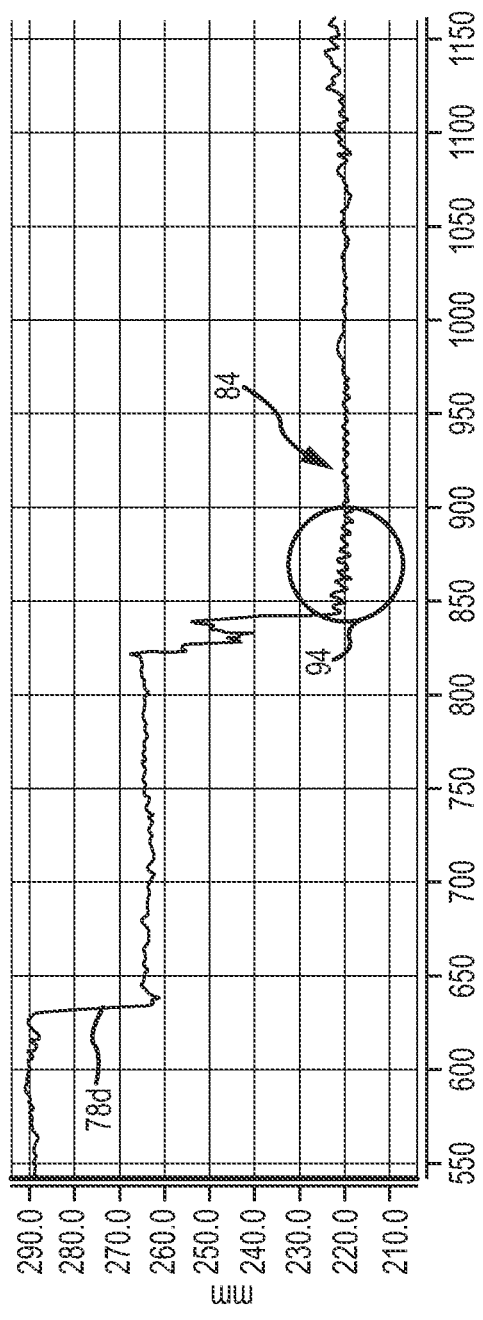

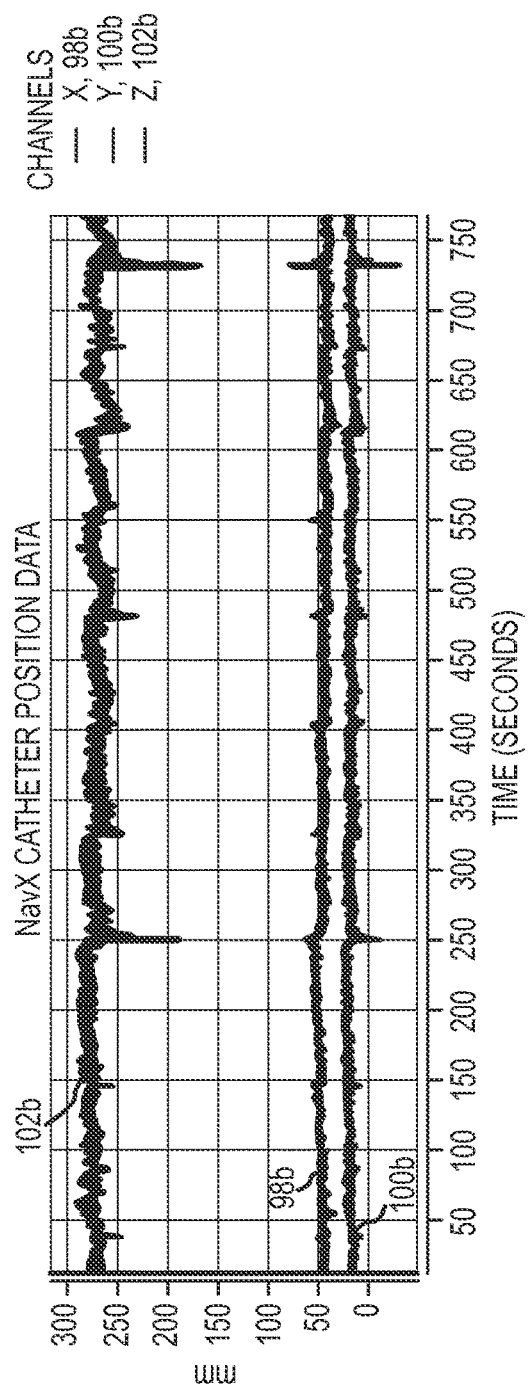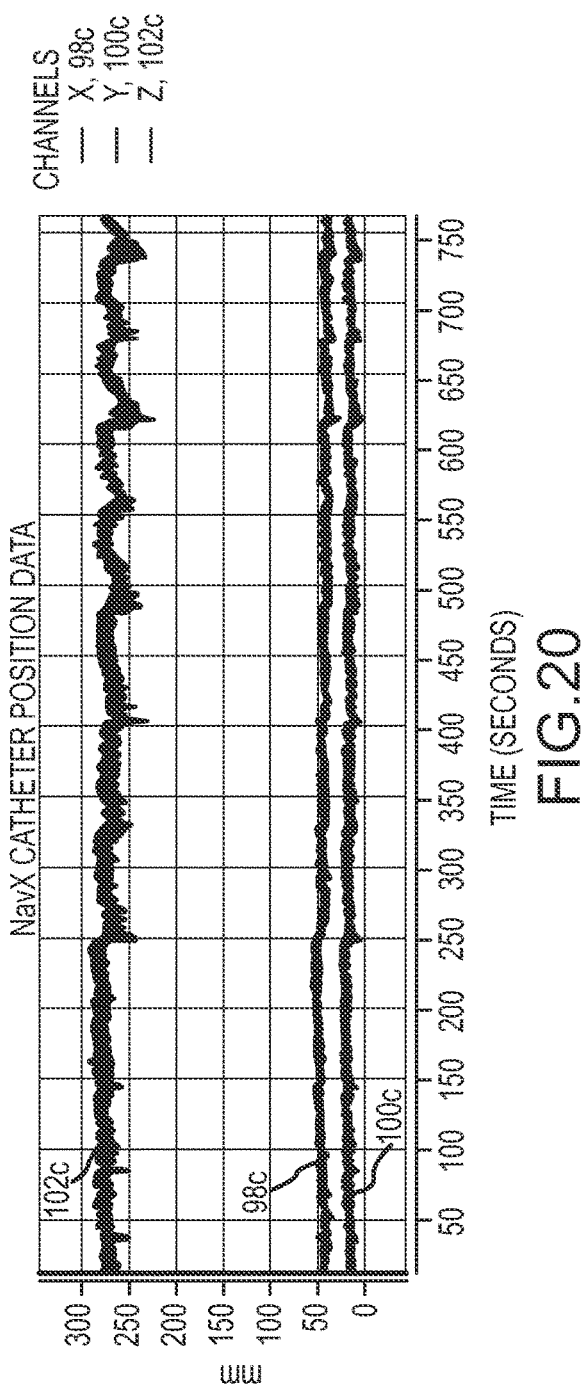

DYNAMIC ADAPTIVE RESPIRATION COMPENSATION WITH AUTOMATIC GAIN CONTROL

CROSS-REFERENCE TO RELATED APPLICATIONS

This application is a divisional of U.S. application Ser. No. 12/980,515, filed 29 Dec. 2010, now U.S. Pat. No. 9,113,807, which is hereby incorporated by reference as though fully set forth herein.

BACKGROUND OF THE INVENTION a. Field of the Invention

The instant invention relates generally to localization systems for determining position utilizing localization fields and more particularly to a localization system having dynamic adaptive respiration compensation with automatic gain control.

b. Background Art

Numerous technologies have been developed to permit the determination of the location of a catheter inside of a beating heart. U.S. Pat. No. 5,697,377 to Wittkampf discloses a system that uses orthogonal currents (i.e., along three axes—X, Y and Z) injected into the body using body surface electrodes (patches) to localize the catheter. In Wittkampf's system, an electrode located on the catheter measures voltages arising from the three injected currents, which are then processed to resolve the X, Y and Z axis coordinates defining the position of the electrode and hence also the position of the catheter tip.

An improved localization system may be seen by reference to U.S. Pat. No. 7,263,397 issued to Hauck et al. (hereinafter "Hauck") entitled METHOD AND APPARATUS FOR CATHETER NAVIGATION AND LOCATION AND MAPPING IN THE HEART, assigned to the common assignee of the present invention, and hereby incorporated by reference in its entirety. Hauck discloses a medical system for determining the location of electrodes within the body utilizing localization fields. Like the system of Wittkampf, the system of Hauck injects currents into the body using surface "patch" electrodes. However, Hauck discloses a variation that involves injecting currents using non-orthogonal pairs of patch electrodes (i.e., defining dipoles) wherein drive axes are synthesized from the resulting measurements and from which the electrode positions are ultimately determined.

A common use of the catheter position is for displaying a representation of the catheter with respect to cardiac geometries or other imaging of a region of interest in which the catheter is located. However, patient respiration and cardiac activity can make the displayed catheter appear to "move" with respect to the acquired cardiac geometries (or imaging), which are static. In order to reduce the apparent motion of the catheter with respect to these static geometries (or imaging) and provide a clinician with a more stable view, it is known to use motion compensation to correct for the effects introduced by patient respiration and cardiac activity.

In this regard, Hauck discloses a respiration compensation approach that involves determining a respiration motion artifact, which in turn is then subtracted from the calculated (uncompensated) electrode position. The respiration compensation method improves accuracy. Hauck further discloses determining the respiration compensation artifact upon a user direction during an electrophysiological (EP) study. In a commercial embodiment, the respiration compensation may be determined at any time but this can be done only at the user's explicit direction. However, during the course of an EP study or medical procedure, a patient's respiration pattern may change or the position of the catheter within the heart may change, such that the previously-determined (static) compensation may no longer provide the initial high level of accuracy. Additionally, during the course of an EP study or medical procedure, there may occur sudden changes in a so-called patch impedance measurement (i.e., a measured parameter underlying the localization and compensation approaches disclosed in Hauck). For example, a clinician may temporarily place his or her hand on a body surface electrode (patch), which temporarily alters the measured patch impedance, thereby affecting the localization/compensation calculations.

There is therefore a need for a system and method for motion compensation (e.g., respiration, cardiac) that minimizes and/or eliminates one or more of the above problems.

BRIEF SUMMARY OF THE INVENTION

One advantage of the methods and apparatus described, depicted and claimed herein involves the ability to provide respiration or other motion (e.g., cardiac activity) compensation for a localization system throughout the duration of an electrophysiological (EP) study or the like despite changing respiration patterns and despite movements of the catheter to different locations in the heart. In addition, an automatic gain control feature mitigates against unwanted interferences introduced by body surface electrode (patch) noise or sudden changes in patch impedance.

A method for determining a compensated location of an electrode of a medical device within a body of a patient may include a number of steps. First, collecting surface (patch) electrode impedance data associated with body surface electrodes and electrode location data associated with the electrode of the medical device. Second, mean-adjusting patch electrode impedance data and the electrode location data. Third, determining an acquired set of weights such that a linear combination of the product of the weights and the mean-adjusted patch impedance data corresponds to the mean-adjusted electrode location data. The fourth step involves repeating (i) the mean-adjusting step and (ii) the acquiring weights step, for a plurality of different time periods and producing a corresponding plurality of sets of weights and updating a reference set of weights as successive sets of weights are acquired. The fifth step involves determining a compensation signal using the updated reference set of weights and patch electrode impedance data. Finally, the last step of the method involves computing a compensated electrode location using an uncompensated electrode location and the compensation signal. In an embodiment, the compensation signal is in-phase with the electrode location and is thus subtracted therefrom to remove the respiration and cardiac artifacts.

The step of acquiring a new set of weights involves, in an embodiment, principal component analysis (PCA) and singular value decomposition (SVD). In addition, the step of updating the reference set of weights involves the use of a learning parameter. The value of the learning parameter is variable and determines how rapidly the reference set of weights (i.e., the set of weights actually used to compute the compensation signal) is adjusted to changes that occur in the new (acquired) set of weights (i.e., the weights computed based on the new patch impedances and electrode location data). A low value for the learning parameter means that the reference set of weights will adapt slowly, while a higher value for the learning parameter means that the reference set of weights will be adjusted aggressively in the direction of the new weights. The learning parameter, in turn, is varied based on a computed "distance" between successive, acquired sets of weights. The "distance" is used to detect when a clinician has intentionally moved the catheter during the calculation of weights, during which dynamic adaptation is suppressed. In addition, the magnitude of the calculated compensation signal may itself be suppressed in accordance with a gain parameter (i.e., an automatic compensation gain control feature). The gain control feature detects when sudden changes occur in the patch impedance data, indicative of noise or the like. In an embodiment, statistical analysis is used to determine when a change constitutes a "sudden" change sufficient to invoke suppression. When such a condition is detected, the gain control feature reduces the gain parameter, thereby reducing the compensation signal.

A corresponding system is also presented.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 10 shows an uncompensated Z-coordinate component of a catheter electrode location containing artifacts as the catheter is moved to different locations within the heart.

FIG. 11 shows the Z-coordinate component of FIG. 10 with applied compensation but without adaptation.

FIG. 12 shows the Z-coordinate component of FIG. 10 with applied compensation but with static adaptation.

FIG. 13 shows the Z-coordinate component of FIG. 10 with applied compensation but with slow adaptation.

FIG. 19 shows the X, Y and Z-coordinate components of FIG. 18, with applied compensation but without gain control where as a result sharp spikes appear in the electrode location data.

FIG. 20 shows the X, Y and Z-coordinate components of FIG. 19 but now with compensation gain control that removes the sharp spikes.

DETAILED DESCRIPTION OF THE INVENTION

Figure 1:
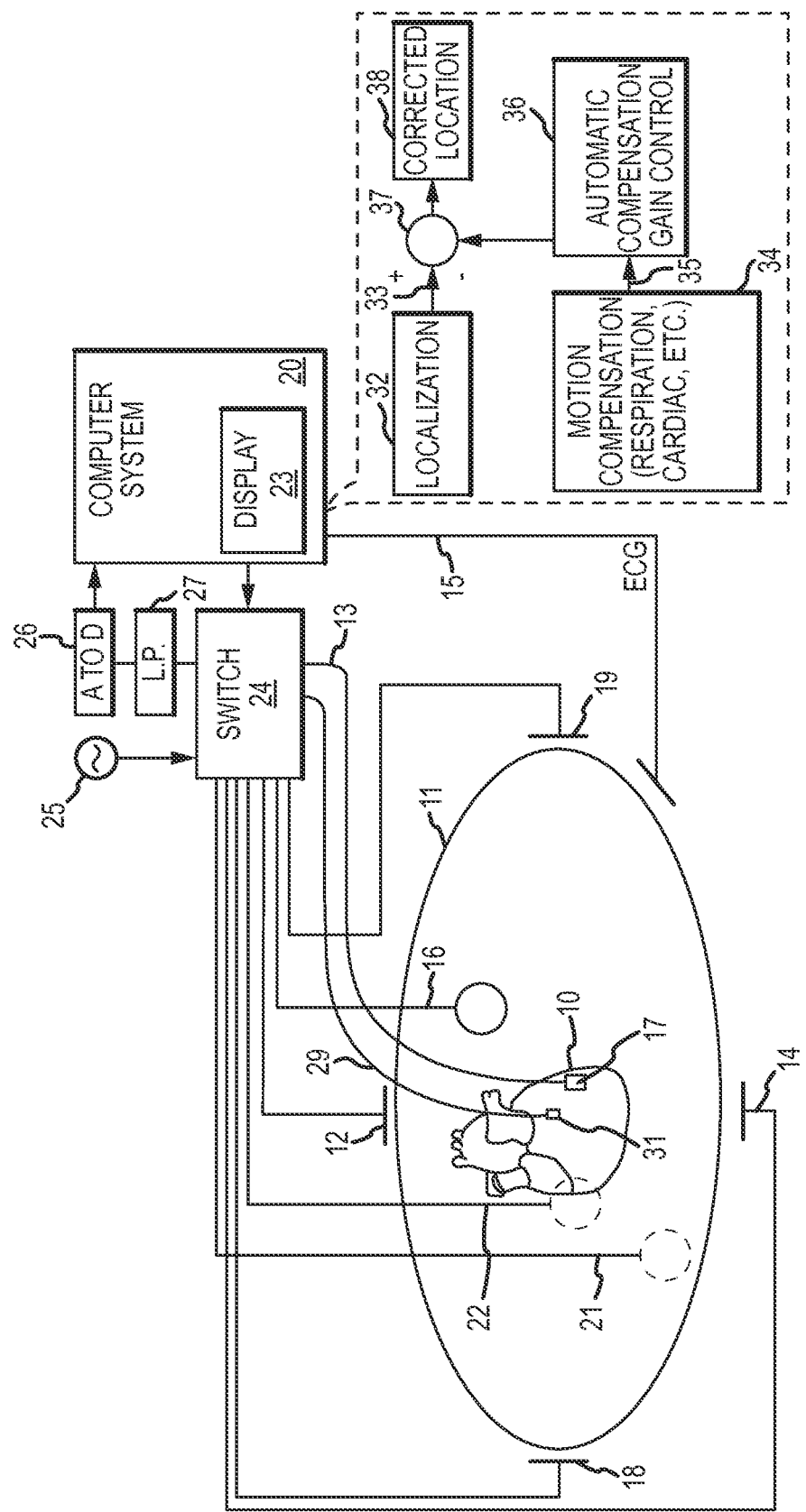
FIG. 1 is a diagrammatic overview of a system in which the invention may be practiced.
Figure 2A:
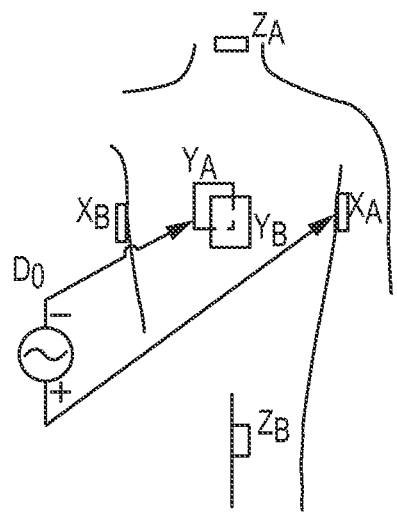
FIGS. 2A-2D are schematic diagrams of dipole pairs of driven body surface electrodes.
Figure 2B:
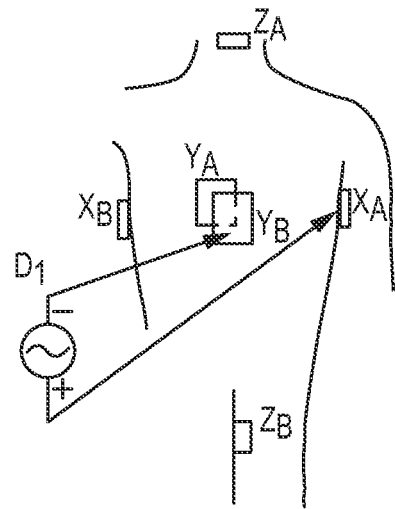
Figure 2C:
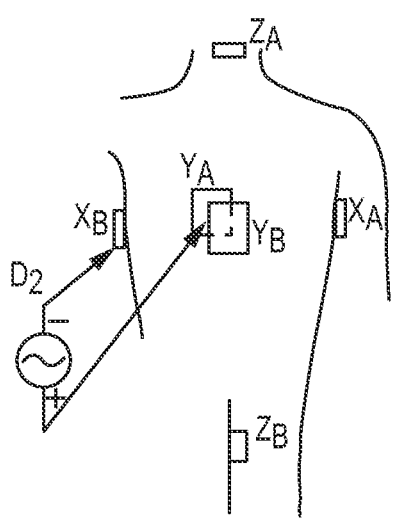
Figure 2D:
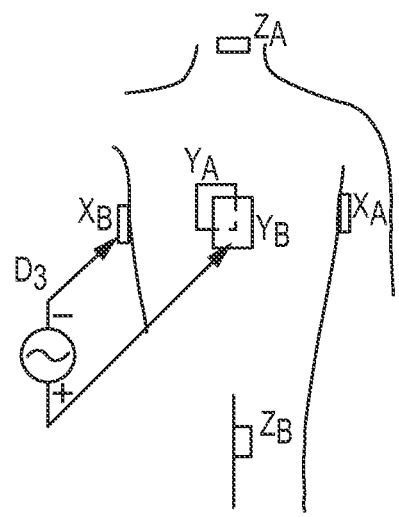

Referring now to the drawings wherein like reference numerals are used to identify identical components in the various views, FIG. 1 is a diagrammatic overview of a catheter system in which the present invention may be practiced. The system may comprise various visualization, mapping and navigation components as known in the art, including among others, for example, an EnSite™ Electro Anatomical Mapping System commercially available from St. Jude Medical, Inc., or as seen generally by reference to U.S. Pat. No. 7,263,397 entitled "METHOD AND APPARATUS FOR CATHETER NAVIGATION AND LOCATION AND MAPPING IN THE HEART" to Hauck et al., or U.S. Patent Publication No. 2007/0060833 A1 to Hauck entitled METHOD OF SCALING NAVIGATION SIGNALS TO ACCOUNT FOR IMPEDANCE DRIFT IN TISSUE, both owned by the common assignee of the present invention, and both hereby incorporated by reference in their entireties. The system may be used in connection with or for various medical procedures, for example, EP studies or cardiac ablation procedures (ablation apparatus not shown). It should be understood that embodiments consistent with the invention may, and typically will, include other features not shown or described herein for the sake of brevity and clarity. For example, when used in connection with an ablation catheter, such an embodiment will typically include various electrodes (and corresponding leads), a temperature sensor (and corresponding leads), and other features as known in the art.

Referring again to FIG. 1, the catheter system includes a diagrammatic depiction of a heart 10 of a patient 11. The system includes the ability to determine a catheter electrode location as the catheter distal end is moved around and within a chamber of the heart 10. For this purpose, FIG. 1 shows a catheter localization system of the type based on externally-applied (i.e., either orthogonal or non-orthogonal) electric fields, which are used to determine the location of one or more catheter electrodes. Such a system is known generally in the art (e.g., an EnSite NAVX™ Navigation and Visualization System mentioned above). It should be understood, however, that this embodiment is exemplary only and not limiting in nature.

With continued reference to FIG. 1, three sets of body surface electrodes (patches) are shown: (1) electrodes 12, 14 (X-axis); (2) electrodes 18, 19 (Y-axis); and (3) electrodes 16, 22 (Z-axis). Additionally, a body surface electrode ("belly patch") 21 is also shown diagrammatically. The surface electrodes are all connected to a switch 24. Of course, other surface electrode configurations and combinations are suitable for use with the present invention, including fewer electrodes, e.g., three electrodes, more electrodes, e.g., twelve, or different physical arrangements, e.g., linear arrangement instead of an orthogonal arrangement.

A representative catheter 13 is also shown, which has a distal electrode 17. The catheter 13 may have additional electrodes in addition to the electrode 17 (e.g., a catheter tip electrode and/or ring electrodes). FIG. 1 also shows a second, independent catheter 29 with a fixed reference electrode 31, which may be stationary on the heart for calibration purposes. In many instances, a coronary sinus electrode or other fixed reference electrode 31 in the heart 10 can be used as a reference for measuring voltages and displacements.

It should be understood that the catheter 13 may include still other electrodes, and in other embodiments, such as in EP or RF ablation embodiments, the other electrodes may be used for any number of diagnostic and/or therapeutic purposes. For instance, such electrodes and therefore such catheters may be used for performing ablation procedures, cardiac mapping, electrophysiological (EP) studies and other procedures. Embodiments of the invention are not limited to any one type of catheter or catheter-based system or procedure.

FIG. 1 further shows a computer system 20, a signal generator 25, an analog-to-digital converter 26 and a low-pass filter 27. The computer system 20 includes a processing apparatus configured to perform many of the functions and operations described herein. The computer system 20 is configured to control the signal generator 25 in accordance with predetermined strategies to selectively energize various pairs (dipoles) of surface electrodes, as described in greater detail below. In operation, the computer system 20 is configured, by way of a localization block 32, to (1) obtain raw patch data (i.e., voltage readings) via the filter 27 and A-D converter 26 and (2) use the raw patch data to determine the raw, uncompensated, electrode location coordinates in three-dimensional space (X, Y, Z) of a catheter electrode positioned inside the heart or chamber thereof (e.g., such as electrode 17).

In an embodiment, most or all of the conventional twelve (12) ECG leads, coupled to body surface electrodes and designated collectively by reference numeral 15, may be provided to support the acquisition of an electro-cardiogram (ECG) of the patient 11. As shown, the ECG leads 15 (if provided) may be coupled directly to the computer system 20 for acquisition and subsequent processing to obtain the phase of the heart in the cardiac cycle. The ECG leads 15 may be also be provided to other systems (not shown).

Each body surface (patch) electrode is independently coupled to the switch 24 and pairs of electrodes are selected by software running on the computer 20, which couples the patches to the signal generator 25. A pair of electrodes, for example the Z-axis electrodes 18 and 19, may be excited by the signal generator 25 to generate a field in the body of the patient 11 and the heart 10. In one embodiment, this electrode excitation process occurs rapidly and sequentially as different sets of patch electrodes are selected and one or more of the unexcited surface electrodes are used to measure voltages. During the delivery of the current pulse, the remaining (unexcited) patch electrodes may be referenced to the belly patch 21 and the voltages impressed on these remaining electrodes are measured by the A-to-D converter 26. In this fashion, the surface patch electrodes are divided into driven and non-driven electrode sets. A low pass filter 27 may process the voltage measurements. The filtered voltage measurements are transformed to digital data by the analog to digital converter 26 and transmitted to the computer 20 for storage under the direction of software. This collection of voltage measurements is referred to herein as the "patch data." The software has access to each individual voltage measurement made at each surface electrode during each excitation of each pair of surface electrodes.

The patch data is used, along with measurements made at electrode 17, to determine a relative location of the electrode 17 in three dimensions (X, Y, Z). Potentials across each of the six orthogonal surface electrodes may be acquired for all samples except when a particular surface electrode pair is driven. In one embodiment, sampling while a surface electrode acts as a source or sink in a driven pair is normally avoided as the potential measured at a driven electrode during this time may be skewed by the electrode impedance and the effects of high local current density. In an alternate embodiment, however, sampling may occur at all patches (even those being driven).

Generally, in one embodiment, three nominally orthogonal electric fields are generated by a series of driven and sensed electric dipoles in order to realize localization function of the catheter in a biological conductor. Alternately, these orthogonal fields can be decomposed and any pair of surface electrodes (e.g., non-orthogonal) may be driven as dipoles to provide effective electrode triangulation.

FIGS. 2A-2D show a plurality of exemplary non-orthogonal dipoles, designated $D_0$, $D_1$, $D_2$ and $D_3$. In FIGS. 2A-2D, the X-axis surface electrodes are designated $X_A$ and $X_B$, the Y-axis surface electrodes are designated $Y_A$ and $Y_B$ and the Z-axis electrodes are designated $Z_A$ and $Z_B$. For any desired axis, the potentials measured across an intra-cardiac electrode 17 resulting from a predetermined set of drive (source-sink) configurations may be combined algebraically to yield the same effective potential as would be obtained by simply driving a uniform current along the orthogonal axes. Any two of the surface electrodes 12, 14, 16, 18, 19, 22 (see FIG. 1) may be selected as a dipole source and drain with respect to a ground reference, e.g., the belly patch 21, while the unexcited body surface electrodes measure voltage with respect to the ground reference. The measurement electrode 17 placed in the heart 10 is also exposed to the field from a current pulse and is measured with respect to ground, e.g., the belly patch 21. In practice, a catheter within the heart may contain multiple electrodes and each electrode potential may be measured separately. As previously noted, alternatively, at least one electrode may be fixed to the interior surface of the heart to form a fixed reference electrode 31, which may also be measured with respect to ground.

Data sets from each of the surface electrodes and the internal electrodes are all used to determine the location of the measurement electrode 17 within the heart 10. After the voltage measurements are made, a different pair of surface electrodes is excited by the current source and the voltage measurement process of the remaining patch electrodes and internal electrodes takes place. The sequence occurs rapidly, e.g., on the order of 100 times per second in an embodiment. To a first approximation the voltage on the electrodes within the heart bears a linear relationship with position between the patch electrodes that establish the field within the heart, as more fully described in U.S. Pat. No. 7,263,397 referred to above.

In sum, FIG. 1 shows an exemplary system that employs seven body surface electrodes (patches), which may be used for injecting current and sensing resultant voltages. Current may be driven between two patches at any time. Measurements may be performed between a non-driven patch and, for example, the belly patch (BP) as a ground reference. A patch bio-impedance, also referred to as a "patch impedance" may be computed according to the following equation:

$$BioZ[n \to m][k] = \frac{V_k}{I_{n \to m}}$$

where $V_k$ is the voltage measured on patch k and $I_{n \to m}$ is a known constant current driven between patches n and m. In one embodiment, time division multiplexing may be used to drive and measure all quantities of interest.

Position Determination.

While U.S. Pat. No. 7,263,397 and Publication 2007/0060833 referred to above (as well as other references) describe position determining procedures generally, a brief outline will none nonetheless be set forth below. The X, Y and Z axes in the body may be defined as follows: (1) X-axis: Right to Left; (2) Y-axis: Back to Chest; and (3) Z-axis: Superior to Inferior (or Cranial to Caudal). This reference coordinate system corresponds to that illustrated in FIGS. 2A-2D.

The location of an electrode (designated e) has X, Y and Z coordinates defined as follows:

$$X[e] = K_x(V^e[L \to B] + V^e[L \to C] - V^e[R \to B] - V^e[R \to C])/2I,$$

$$Y[e] = K_y(V^e[L \to C] + V^e[R \to C] - V^e[L \to B] - V^e[R \to B])/2I,$$

$$Z[e] = K_z(V^e[N \to B] - V^e[LLeg \to B])/I,$$

where $K_x$, $K_y$, and $K_z$ are fixed coefficients converting impedance readings (patch impedances) to positions and $V^e[n \to m]$ are voltages measured by the system between the catheter electrode (e) and the ground reference, for example the belly patch 21, when current is driven between patches n and m. The measurement of position is thus indirect and involves algebraic combination of various measurements to derive positions of the electrodes and the patch impedances related to the X, Y and Z axes defined in the body.

With continued reference to FIG. 1, the computer system 20 includes a localization block 32, which is configured to generate an uncompensated location (signal or parameter) of an electrode (i.e., designated as signal or parameter 33 in FIG. 1). In one exemplary embodiment, the localization block 32 may employ the energizing, voltage measuring and data processing strategies as outlined above and/or as described in U.S. Pat. No. 7,263,397 or U.S. Patent Publication 2007/0060833. The electrode location 33 may contain a position, an orientation or both, where the position in turn may have X-axis, Y-axis and Z-axis coordinates or components, defined for a reference coordinate system.

The computer system 20 further includes a motion compensation block 34 configured to generate a compensation signal (or parameter), designated as signal (or parameter) 35 in FIG. 1, suitable for minimizing or eliminating motion artifacts (e.g., respiration, cardiac, etc.) contained in the electrode location 33. In an embodiment, the compensation block 34 may employ methodologies as described herein in accordance with various embodiments, such as the principal component analysis-based approach described below.

The system 20 further includes an automatic compensation gain control block 36 configured to selectively suppress the compensation signal 35 when certain conditions are met. The system 20 further includes a mechanism, e.g., a summer 37 as shown diagrammatically in FIG. 1, to subtract in-phase compensation signal 35 from the uncompensated electrode location signal 33 to produce a corrected or compensated electrode location signal 38.

As described in the Background, respiration and cardiac activity make catheters appear to move with respect to cardiac geometries (or pre-acquired imaging), which appear static in nature. In order to reduce the apparent motion of the catheters (e.g., to provide a clinician with a more stable view of the catheter in the cardiac chamber), a compensation function is used, as produced by the compensation block 34. In a prior system, respiration compensation was computed at a user-selected time during an electrophysiological (EP) study (e.g., typically at the beginning) and thereafter remained unchanged unless the user specifically commanded the system to re-compute the compensation. The approach thus did not provide a mechanism for automatically adapting to changing respiration patterns, movement of the catheter to different locations in the heart, or sudden changes in patch impedances.

As described above, embodiments of the invention generally address the problem of respiratory and cardiac artifacts by subtracting a compensation signal, which corresponds to the undesired respiration and cardiac artifacts, from an electrode's uncompensated location, so that only the true location of the catheter will be visible, e.g., when displayed.

The compensation signal 35 is thus preferably a signal indicative of or that reflects the respiratory/cardiac artifacts, and is generated (or modified) to be both (i) in-phase and (ii) of an adequate amplitude to substantially nullify the respiratory and/or cardiac artifacts contained in an electrode's location over time.

Compensation Using Patch Impedance Data.

As will be described below, embodiments of the invention use a best fit combination of the acquired patch impedance data to produce a useful respiration compensation signal. In one aspect, the compensation is dynamically adapted to changes in the underlying conditions (i.e., respiration patterns, location of the catheter). Another aspect involves a compensation gain control feature, which operates to limit the amount of applied compensation when patch impedances experience sudden changes.

Before proceeding, a few observations as to the nature of the artifacts being compensated. First, in general, respiration artifacts have greater time periods than cardiac artifacts. Second, the majority of the respiration and cardiac motions are contained in the Z axis (i.e., the axis running roughly between the patient's feet and head), with the rest occurring in the X and Y axes.

As described above, the system 20 collects a plurality of patch impedances, the particular number of which depends on the embodiment (e.g., there are up to 36 non-zero patch impedances in one embodiment, while up to 24 patch impedances in another embodiment). These patch impedances are collected in a substantially continuous fashion. The respiration and cardiac motion artifacts may appear more strongly on some patch impedances (i.e., the patch impedances of a particular patch measured over time). Additionally, not all patch impedances measured over time (a patch "channel") exhibit noticeable artifacts. The artifacts that are present in some of the different patch channels, however, are present with the same phase as the artifacts in the electrode location signal. This allows the artifacts appearing in the patch impedances to be used to create the compensation signal, which can then be subtracted, assuming the proper amplitude has been determined, from the electrode location signal to cancel the artifacts. The fact that the phase of the reference information upon which the compensation signal is produced does not have to be adjusted allows for a relatively straightforward method.

The methods described herein involve determining an optimal linear combination of acquired patch impedance data that substantially cancels the motion artifacts of a given electrode's location over time. It bears mentioning that in the description below, each axis of each electrode for which compensation is to be applied is determined separately. In some embodiments, fewer than all three axes may be compensated, and in one embodiment only one axis is compensated (e.g., the most severely affected—Z-axis). With that being said, the mathematical notation that will be used to describe the methods will now be set forth below.

Let X be a catheter electrode's coordinate with samples $X_i$, where a lower index i describes time samples of the variable X. Thus, X may be viewed as a vector in the N-dimensional space, where N is the number of the time samples collected.

Let $P^j$ be patch impedances, with an upper index j=1, ..., M that numbers different patch pairs with M being the number of different patch pairs. Then $P_i^j$ represent time samples of patch impedances, which makes it an N×M matrix (here i numbers the rows and j numbers the columns).

The framework described herein assumes that if a catheter with an electrode under consideration is not intentionally moved, then the only motion of the electrode would be due to respiratory and cardiac artifacts, which may be described by the electrode position coordinate X with its mean value thereof subtracted:

$$\tilde{X} = X - \text{mean}(X). \quad (1)$$

where $\tilde{X}$ is the mean-adjusted electrode location coordinate.

Similarly, the respiration and cardiac artifacts contained within the patch impedance data will be described by the patch impedance data with its mean value thereof subtracted:

$$\tilde{P}^j = P^j - \text{mean}(P^j). \quad (2)$$

where $\tilde{P}$ is the mean-adjusted patch impedance data.

The mean function in Equations (1) and (2) may be, in one embodiment, a moving average assessed over a window of a predetermined size. Such a window may be selected to be long enough to average out both respiration and cardiac artifacts. For example only, a three (3) second window may be effective to average out cardiac activity while a fifteen (15) second window may be effective to average out respiratory motion. Of course, the specific length of the window for each artifact will depend on the desired level of motion artifact removal/filtering. Accordingly, the values defined by Equation (1) may be considered as containing only the motion artifacts to be compensated.

To cancel the artifacts, a linear combination of patch impedances has to be found that satisfies equation (3):

$$\tilde{X}_i = \sum_{j=0}^{M} \tilde{P}_i^j \cdot W^j, \quad (3)$$

where $W^j$ is a set of M "weights" with which the patch impedances have to be taken to cancel the artifacts. The weights are found as solutions to the Eq. (3) and have to be specific for each axis of every electrode for which the compensation is computed (i.e., the equation (3) addresses one axis for one electrode). For each axis of each electrode there are up to M independent weights.

It should be appreciated that Equation (3) contains as many equations as there are samples in the signals, and if the number of samples exceed the number of patch impedances, it could be significantly over-determined (i.e., there would be redundancy in the data and so the result obtained from an over-determined system can be more robust). For example, at the sampling rate of 100 Hz and window size of 10 seconds, one would have 1000 equations for only about 24 independent weights (i.e., for an embodiment having 24 different nonzero patch impedances). Therefore, in one embodiment, Equation (3) may be solved by minimizing an error as per equation (4) below:

$$\varepsilon = \left\| X_i - \sum_{j=0}^{M} \tilde{P}_i^j \cdot W^j \right\| \quad (4)$$

The solution minimizing the error is given by the Singular Value Decomposition (SVD). The mathematical technique has a very profound physical meaning as it is related to the so-called Principal Component Analysis (PCA) that will be described below.

Principal Component Analysis (PCA) of Patch Impedance Data.

Principal component analysis (PCA) aims at finding the directions in the vector space of functions in which the analyzed functions are most similar to each other, while sharing the most striking common features. The patch impedance data and the electrode location data can be viewed as similar, at least with respect to the fact that they both contain respiration and cardiac artifacts. Collected patch impedance data and catheter (electrode) location data may be viewed as vectors in the $R^N$ N-dimensional vector space, where N is the number of samples used in the computation. As samples are acquired over a period of time, the vectors represent the waveforms. Similar waveforms (most correlating) are similar to vectors pointing in the same direction, having the greatest projections on each other. If one can find a direction on which the most vectors have predominantly greatest projections, this direction may be used for characterization of the most important features of the signals encoded by the waveforms. In turn, the vector pointing in that direction may be considered as a waveform itself, and will resemble the most striking features of the analyzed signals, and which direction may be referred to as the First Principal Component of the analyzed signal. After the direction associated with the most pronounced features is found, one can repeat the analysis on the vectors with the parts along the First Principal Component subtracted, or in other words, in the subspace of dimension N−1 orthogonal to the first principal component. This next direction in the functional vector space will correspond to the Second Principal Component. The procedure can be repeated to find all other principal components, of which there will be as many as many vectors are being analyzed.

In an embodiment, the principal components of the patch impedances serve as references for compensation of similar signals in all the electrode location data. The mathematical technique for the PCA is given by the Singular Value Decomposition (SVD), in which an arbitrary matrix A is represented as a product of three matrices:

$$\tilde{P} = USV^T, \quad (5)$$

where:

$\tilde{P}$ is the analyzed N×M matrix (columns are patch impedances in our case), U is the orthogonal N×M matrix which columns represent the principal components of the columns of the matrix $\tilde{P}$, S is an M×M diagonal matrix containing the so-called singular values, showing relative contributions of the principal components to the patch signals:

$$S = \begin{pmatrix} S_1 & 0 & 0 & \dots \\ 0 & S_2 & 0 & \dots \\ 0 & 0 & S_3 & \dots \\ \dots & \dots & \dots & \dots \end{pmatrix}, S_1 > S_2 > S_3 > \dots ,$$

V is an M×M orthogonal matrix with columns containing relative contributions of each column of $\tilde{P}$ (corresponding to contributions of different patches) to the corresponding principal component. This property of the matrix V could be seen from the following explicit expressions, which follow from Eq. (5):

$$U_{1j} = \frac{1}{S_j} \left( \tilde{P}_1^1 * V_{j1} + \tilde{P}_1^2 * V_{j2} + \tilde{P}_1^3 * V_{j3} + \dots \right) \quad (6)$$

$$U_{2j} = \frac{1}{S_j} \left( \tilde{P}_2^1 * V_{j1} + \tilde{P}_2^2 * V_{j2} + \tilde{P}_2^3 * V_{j3} + \dots \right)$$

$$U_{3j} = \frac{1}{S_j} \left( \tilde{P}_3^1 * V_{j1} + \tilde{P}_3^2 * V_{j2} + \tilde{P}_3^3 * V_{j3} + \dots \right)$$

...

For example, the first equation expresses the first sample of the jth Principal Component as a sum of the first samples of different patches taken with the coefficients from the matrix V. So, the first column of V provides the coefficients for the first patch, the second column of V for the second patch and so on.

If the SVD of the matrix $\tilde{P}$ is known, then the matrix could be "inverted" in the following sense: one can compute $$V \cdot S^{-1} \cdot U^T \quad (7)$$

where $$S^{-1} = \begin{pmatrix} \frac{1}{S_1} & 0 & 0 & \dots \\ 0 & \frac{1}{S_2} & 0 & \dots \\ 0 & 0 & \frac{1}{S_3} & \dots \\ \dots & \dots & \dots & \dots \end{pmatrix}, \quad (8)$$

for nonzero $S_i$ and the diagonal elements are left zeros if they are equal to zero. This procedure is known as taking a pseudo inverse of the matrix $\tilde{P}$ and is configured to minimize the error in equation (4). In the case when some of the singular values $S_i$ have small non-zero values, this procedure may result in very large diagonal elements of the $S^{-1}$, leading to hypersensitivity of the results on small variations in the input data. In that case, a regularization procedure may be used, by which the corresponding diagonal elements are set to zero. In practical embodiments, this means that not all of the principal components are used in the computation, but only a subset of them that contains the majority of the information present in the data. Small singular values may indicate that a corresponding principal component contains mostly noise and can be neglected.

Figure 3:
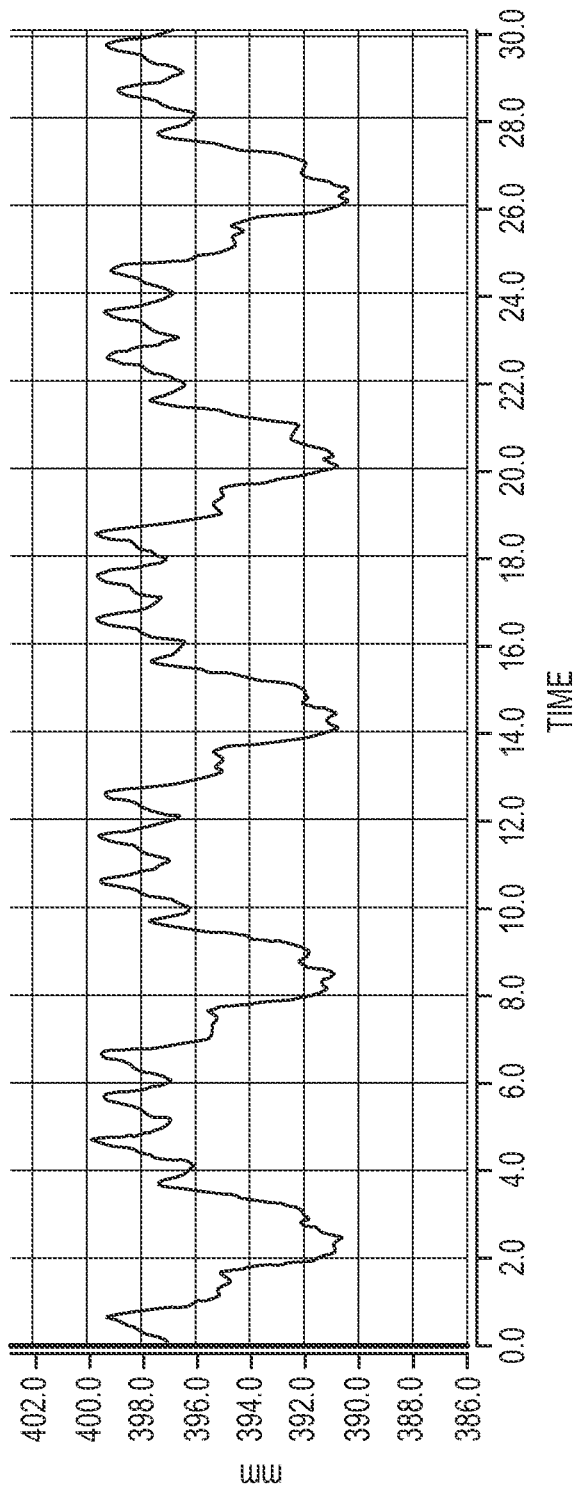
FIG. 3 shows an uncompensated Z-coordinate component of a catheter electrode location containing respiratory and cardiac artifacts.
Figure 4:
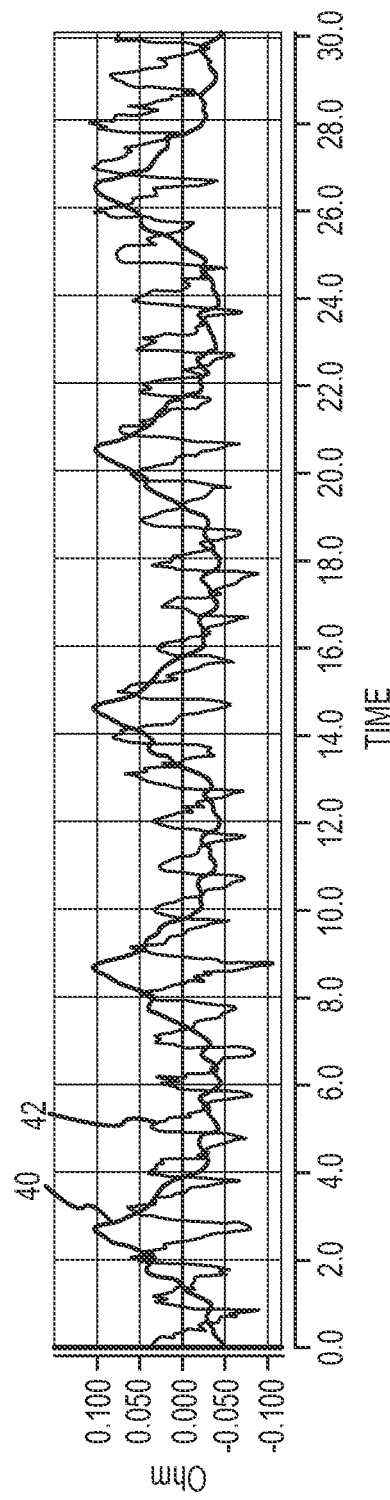
FIG. 4 shows the first two principal components of patch impedances (corresponding to FIG. 3) obtained with a singular value decomposition (SVD) technique.
Figure 5:
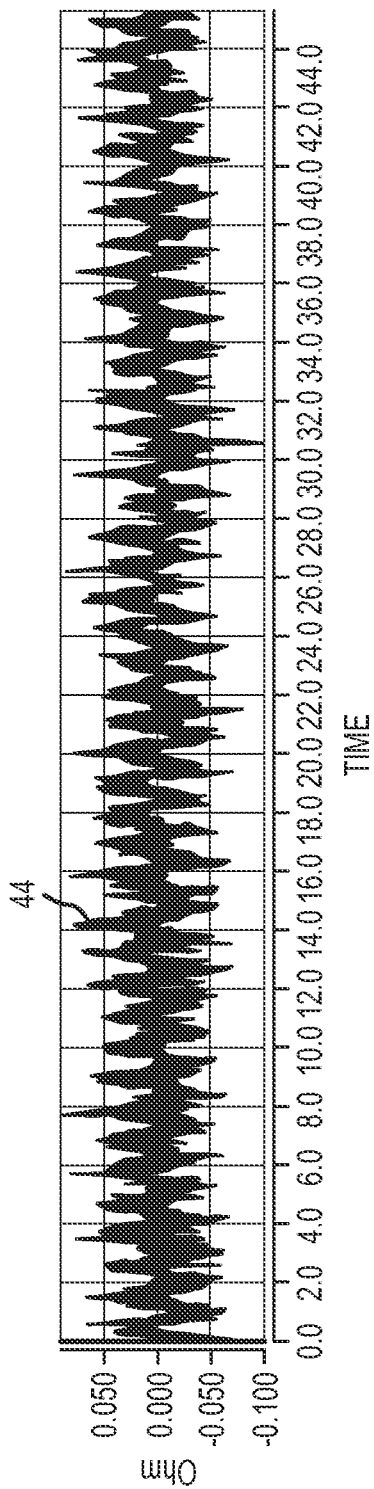
FIG. 5 shows a third principal component containing cardiac artifacts and noise.

FIGS. 3-5 illustrate the first three principal components of patch impedance data. FIG. 3 in particular is a displacement versus time plot showing an uncompensated location (Z-axis coordinate) of a catheter electrode containing respiratory and cardiac artifacts.

FIG. 4 is patch impedance versus time plot showing the corresponding (i.e., corresponding to the electrode location of FIG. 3) first two principal components of the patch impedances. The plots illustrated in FIG. 4 were obtained with a singular value decomposition (SVD) technique described above as applied to the patch impedance data. A first trace 40 is the first principal component, which resembles the respiratory artifacts contained in the electrode motion of FIG. 3. A second trace 42 is the second principal component, which resembles the cardiac artifacts contained in the electrode motion of FIG. 3.

FIG. 5 is a plot of patch impedance versus time, designated as trace 44, showing a third principal component of the patch impedance data. The trace 44 contains cardiac artifacts along with some noise. While in this example, principal components of higher order most closely resemble only noise, in one embodiment, such higher orders are not completely neglected, as the noise they contain is correlated with the electrode locations, and inclusion of them compensates some of that noise. In an embodiment, all orders may be used since the identification of what orders will be important may be difficult to determine a priori.

Once Eq. (3) has been solved for a set of weights $\{W^j\}$, the method calls for using the set of weights to continuously correct an uncompensated electrode location (e.g., on a per-axis basis, in one embodiment). For example, such continuous correction may be performed in accordance with Eq. (10) below (i.e., by subtracting weighted sums of patch impedances from the respective X, Y and Z axis coordinates). As described above, this method may also be extended to each electrode for which compensation is being applied (each electrode being compensated for on an axis-by-axis basis, in an embodiment).

In Eq. (3), X is used as a generic symbol denoting any of the X, Y or Z axis projections of any electrode. It bears emphasizing that for each projection of each electrode, a respective set of weights used in the Eq. (10) must be computed individually by minimizing the error as per Eq. (4), according to the Equation (9) below:

$$W = V \cdot S^{-1} \cdot U^T \cdot \tilde{X}, \quad (9)$$

where the results of the singular value decomposition (SVD) of the patch impedance matrix of Equation (5) may be used. Note that Eq. (9) is written in matrix form, so all indices are suppressed. Patch impedance and electrode location data used in the computation of weights are preferably collected over a predetermined period of time that includes some minimum number of the respiration cycles. The number of relevant singular values used in Eq. (9) was found, in one embodiment, to be ~15. After the weights have been computed per Eq. (9), they may be used for continuous correction of the electrode location as per equation (10):

$$X_i^{jcorrected} = X_i - \sum_{j=0}^{M} \tilde{P}_i^j \cdot W^j, \quad (10)$$

The compensation block 34 (FIG. 1) configured to generate a compensation signal (i.e., rightmost term above in Eq. (10)) may in one embodiment, be configured to perform the steps described above. The overall method of determining a location of an electrode that is compensated for respiratory and cardiac artifacts may be summarized as follows:

The first step involves collecting patch impedance data P and electrode location data X for a time period of T seconds.

Second, subtracting the computed mean from both the patch impedance and electrode location data to obtain mean-adjusted patch impedance data $\tilde{P}$ and electrode location data $\tilde{X}$, as set forth below:

$$\tilde{P}=P-\text{mean}(P),$$

$$\tilde{X}=X-\text{mean}(X).$$

The next (third) step involves performing singular value decomposition (SVD) of the mean-adjusted patch impedance data $\tilde{P}$:

$$\tilde{P}=U \cdot S \cdot V^T$$

The fourth step involves taking the pseudo-inverse of $\tilde{P}$ and applying regularization (e.g., using the first ~15 singular values in one embodiment), as set forth below:

$$\tilde{P}^{-1}=V \cdot S^{-1} \cdot U^T$$

The fifth step involves computing, for each axis for which compensation is being applied, a respective set of weights W according to the expression below:

$$W=V \cdot S^{-1} \cdot U^T \cdot \tilde{X}$$

The sixth (final) step involves correcting an uncompensated electrode location, on a per-axis basis, using the respective sets of weights, as set forth below:

$$X_i^{jcorrected} = X_i - \sum_{j=0}^{M} \tilde{P}_i^j \cdot W^j$$

Note, that the above method involves one singular value decomposition step, the result of which is then applied to all axes of all electrodes. As emphasized, the correction expression immediately above is applicable to an axis (e.g., X, Y or Z) for which compensation is being applied. To the extent multiple axes are being compensated, then a respective set of weights for that axis would be used.

Figure 6:
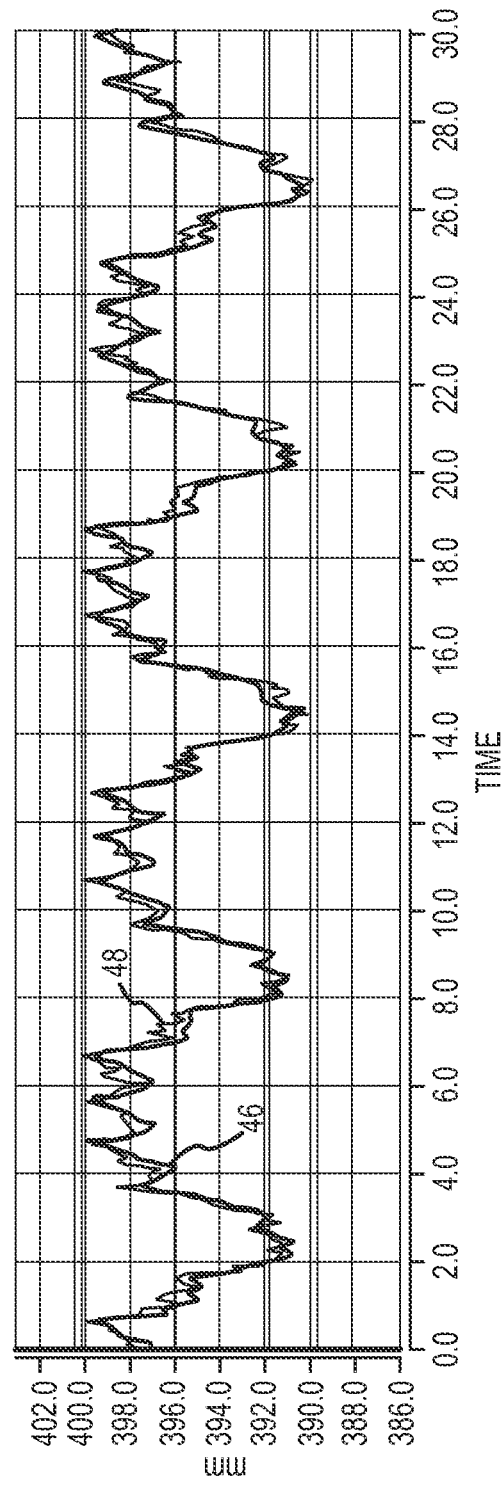
FIG. 6 shows an uncompensated Z-coordinate component and a calculated compensation signal overlaid on the same timeline.

FIG. 6 shows an uncompensated electrode location (Z-axis coordinate), plotted over time (trace 46). Trace 46 corresponds to the uncompensated signal shown in FIG. 3. In addition, FIG. 6 shows a compensation signal, designated as trace 48, calculated in accordance with the above methodology and overlaid on the same timeline as trace 46.

Figure 7:
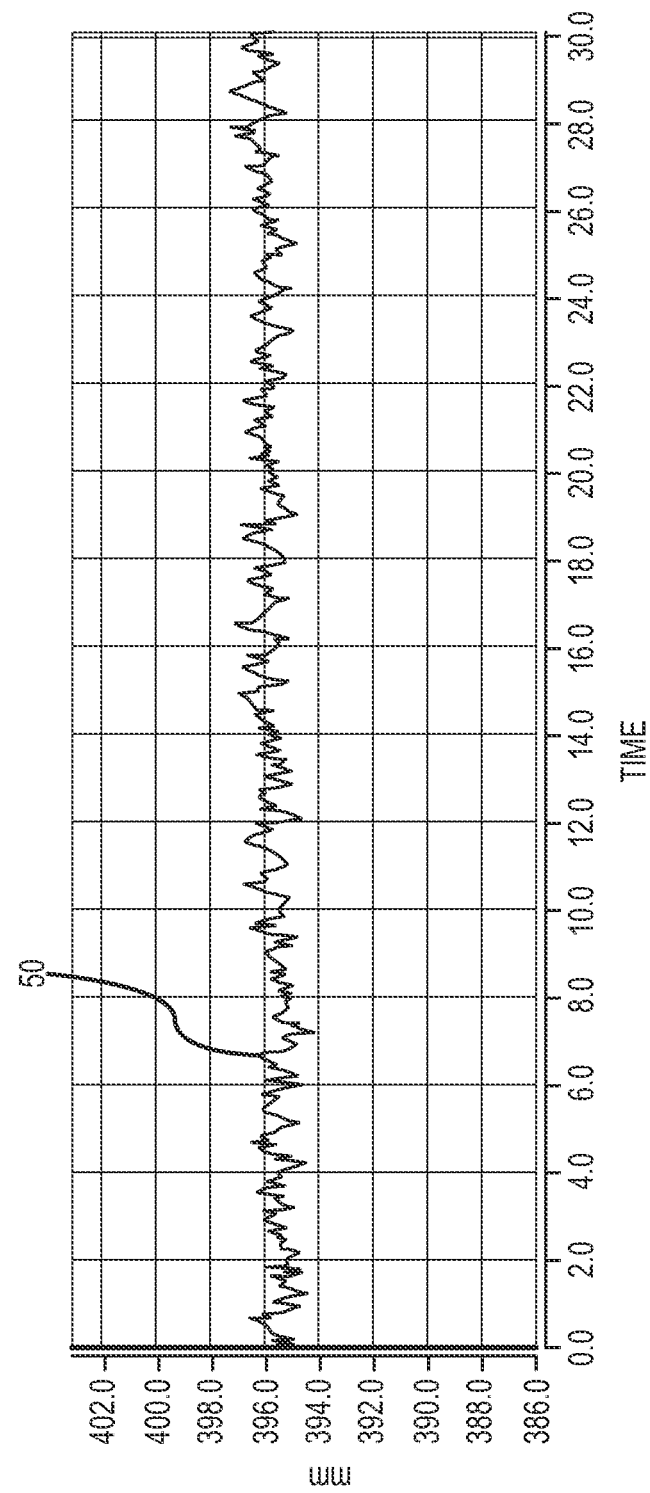
FIG. 7 shows the Z-coordinate component compensated to remove artifacts.

FIG. 7 is a displacement versus time plot (Z-axis coordinate) showing the results of subtracting the compensation signal from the electrode location signal of FIG. 6. The trace 50 is the compensated electrode location signal. FIG. 7 demonstrates that the compensation approach described herein not only addresses the respiration artifacts but also the bulk of the cardiac artifacts as well. In an embodiment, any remaining cardiac artifacts in FIG. 7 may be reduced or eliminated by the system 20 using a relatively fast low pass filter.

In the compensation method described above, a set of weights is computed at a selected time during an electrophysiological (EP) study, which may thereafter be used, or until the user commands that the weights be recomputed. The originally computed set of weights, however, may not remain optimal after some time has passed. This may occur, for example, when the patient's respiration pattern changes (i.e. and is thus different than the respiration pattern upon which the original set of weights/compensation signal was determined). The set of weights, in addition, may no longer remain optimal when the catheter has been moved to a different location inside the heart. In either instance, a new set of weights would be desirable. While the method may be repeated manually to obtain a new set of weights, in such instance it would be up to the clinician to determine when that is needed. This may be impractical for a number of reasons (e.g., if the clinician is in the midst of a procedure, if the clinician cannot detect a change in breathing patterns, etc.).

Adaptive Compensation (Static).

In an embodiment, an adaptive method for compensation is provided. In this embodiment, new data is acquired and a new set of weights $W_n$ is computed at regular time intervals (e.g., 1 sec to 1 minute). The method updates the reference set of weights using the new weights $W_n$ as each successive set of new weights is acquired, in accordance with Eq. (11):

$$W \leftarrow W + \lambda^*(W_n - W), \quad (11)$$

where a learning parameter $\lambda$ (where $0 < \lambda \leq 1$) determines the rate at which the new acquired set of weights $W_n$ updates the current or reference set of the weights W. The reference set of weights is the set used to calculate the compensation signal.

Equation (11) specifies that the reference set of weights is continuously shifted in the functional space in the direction of the newly computed weights $W_n$. To develop intuition with the adaptive methodology, Equation (11) may be re-written in an exponential moving average form as per equation (12):

$$W \leftarrow (1-\lambda)^* W + \lambda^* W_n. \quad (12)$$

The reason the learning parameter is valued between 0 and 1 is that when the learning parameter is set to one (1), the system 20 may be prone to magnifying potential transient artifacts of the patch impedances themselves, while when the parameter is set too small (e.g., zero), the system 20 would adapt too slowly or not at all to new conditions.

One challenge with using a static adaptation rule such as set forth in Eq. (11) is that if the catheter is moved during the acquisition of data leading to the computed set of weights, such a movement could be coupled to the patch signals (i.e., the measured patch impedances), in turn producing an incorrectly computed set of weights. The incorrect set of weights could produce unpredictable results as the new set of weights would try to compensate for the intentional movement of the catheter.

One approach to address the above challenge involves assigning the learning parameter $\lambda$ a small value, thus effectively averaging out the catheter motion, while accumulating the respiration compensation information over long time. However, a disadvantage of such an approach is slow adaptation to respiration changes and the like.

Adaptive Compensation (Dynamic Adaptation).

Another approach to address the above challenge involves dynamically adapting the learning parameter. The dynamic adaptation is effective to counter the issue of coupling intentional catheter motion to the patch signals. In the intentional movement situation, the dynamic adaptation would operate to set the learning parameter to small values when catheter motion is detected, adapting little (if at all)

when the catheter is moved. Likewise, when the catheter is not moved, the dynamic adaptation would provide for aggressive adaptation of the learning parameter toward its maximum value.

Dynamic adaptation of the learning parameter may be based on knowing when the catheter is being intentionally moved by a physician. However, this knowledge may not always be available. Accordingly, as an alternative, the learning parameter λ itself is adjusted based on how much change occurs between successively computed sets of weights. The underlying assumption is that the weights will not change too drastically during normal operation if the catheter is not being intentionally moved. Thus, the system is configured to monitor the rate of change of the weights, and if the weights change significantly (i.e., exceeding a threshold), then the learning parameter is set to relatively low values, thereby suppressing adaptation. However, if the amount of change does not exceed the threshold, then the learning parameter λ is set close to its maximum value, thus quickly adapting to reflect the newly calculated ($W_n$) set of weights.

In one embodiment, the value for the learning parameter may be set according to the Eq. (13) below:

$$\lambda = \lambda_{max} \exp(-(\|W_o - W_n\|^2 / (\|W\|_{min}^2 \gamma^2))) \quad (13)$$

where $W_n$ corresponds to the set of weights computed on the most-recent step ("new" acquired set of weights);

$W_o$ corresponds to the set of weights computed during the previous step ("old" acquired set of weights);

$\|W\|^2$ is the sum of squares of all weights;

$\|W\|_{min}^2$ is the minimum sum of squares of weights $\|W_o\|^2$ and $\|W_n\|^2$; and, γ defines the distance, in the functional space, by which the weights must be different for the adaptation to be suppressed.

When the distance between successive sets of weights becomes larger than γ, the learning parameter λ is exponentially suppressed and the weights are effectively not updated. For example, in one embodiment, suitable results were obtained where the data collection time period T=3 seconds, the maximum value for the learning parameter was set to $\lambda_{max}=1$ and the value for $\gamma^2$ was set in the range between 1 and 2. It should be understood that variations of Eq. (13) are possible, for example, functions other than the exponential function (exp) may be used to suppress or reduce the value of the learning parameter, based on the distance between successive sets of weights.

Figure 8:
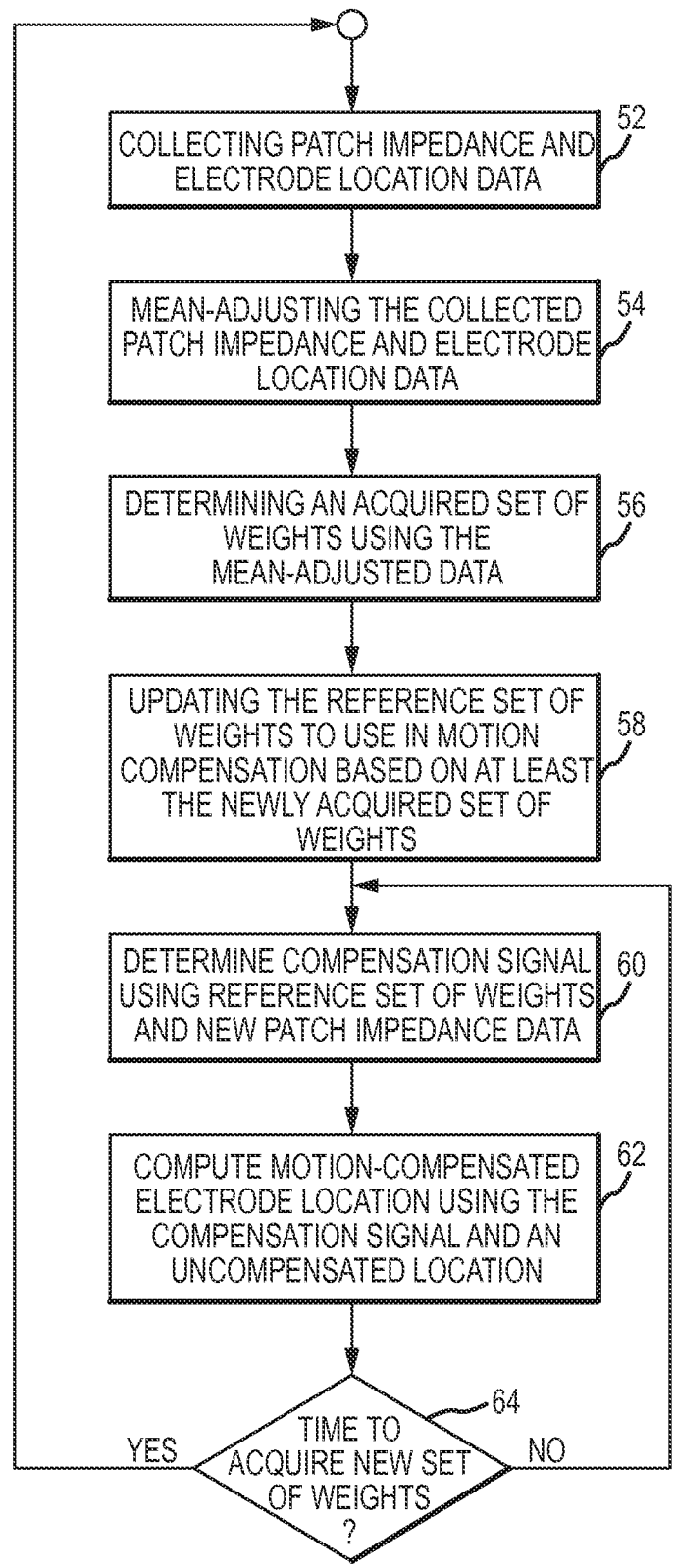
FIG. 8 is a flowchart diagram showing a method for determining an electrode location having dynamic compensation.

In view of the foregoing, FIG. 8 shows a method for determining an electrode location having dynamic adaptive respiration compensation. The method begins in step 52.

In step 52, the method first involves collecting patch electrode impedance data as well as electrode location data. This step may be performed substantially as described above. In addition, it bears emphasizing that the methodology as described above will be performed for each axis of each electrode that is selected to receive respiration and/or cardiac compensation. The method then proceeds to step 54.

In step 54, the method then involves mean-adjusting the collected patch electrode impedance and electrode location data, which step may be performed substantially as described above and in particular as set forth in equations (1) and (2). After the step of mean-adjusting, the resultant vectors should contain principally respiratory and cardiac artifacts. The method then proceeds to step 56.

In step 56, the method involves determining an acquired set of weights using the mean-adjusted data from step 54. This step may be performed substantially as described above, and which may involve performing singular value decomposition (SVD) in order to minimize an error such that the sum of the product of the mean-adjusted patch data and the weights correspond to the mean-adjusted electrode data (Eq. (3)). In other words, the undesired respiratory and cardiac artifacts found in the mean-adjusted electrode location data are also found, in-phase, in the mean-adjusted patch electrode impedance data. Accordingly, some combination of weights of the patch data may be used to compute a compensation signal, which can be subtracted from the electrode location data to obtain a compensated electrode location. The method then proceeds to step 58.

In step 58, the method involves updating a reference set of weights, destined for use in computing the compensation signal, using the newly-acquired set of weights. This step may be performed substantially as described above, particularly in connection with equation (11). In a preferred embodiment, this step includes the sub-step of dynamic adaptation of the learning parameter (Eq. (13) and FIG. 9). The method proceeds to step 60.

In step 60, the method involves determining the compensation signal using the updated reference set of weights from step 58 as well as patch impedance data. This step may be performed substantially as described above, and in particular as described in connection with equation (10). Specifically, the right-most term in equation (10) defines the respiration compensation signal:

$$\sum_{j=0}^{M} \tilde{P}_i^j \cdot W^j.$$

The method proceeds to step 62.

In step 62, the method involves computing an electrode location substantially free of respiratory and cardiac artifacts, by subtracting the computed compensation signal from step 60 from an uncompensated electrode location. The method proceeds to step 64.

In step 64, the method evaluates whether it is time to acquire a new set of weights. This decision may be based on a predetermined time period set to acquire a new set of weights for updating the reference set of weights. If the answer in step 64 is "NO," then the method branches back to steps 60 and 62 where the method continuously corrects electrode locations based on the compensation signal. However, if the answer given in step 64 is "YES," then the method branches to the beginning in step 52. It should be understood that the flowchart of FIG. 8 is exemplary only and not limiting in nature. For example, the step of collecting patch impedance and electrode (location) data may be performed within system 20 for other purposes even if the "YES," branch is not taken in step 64.

Figure 9:
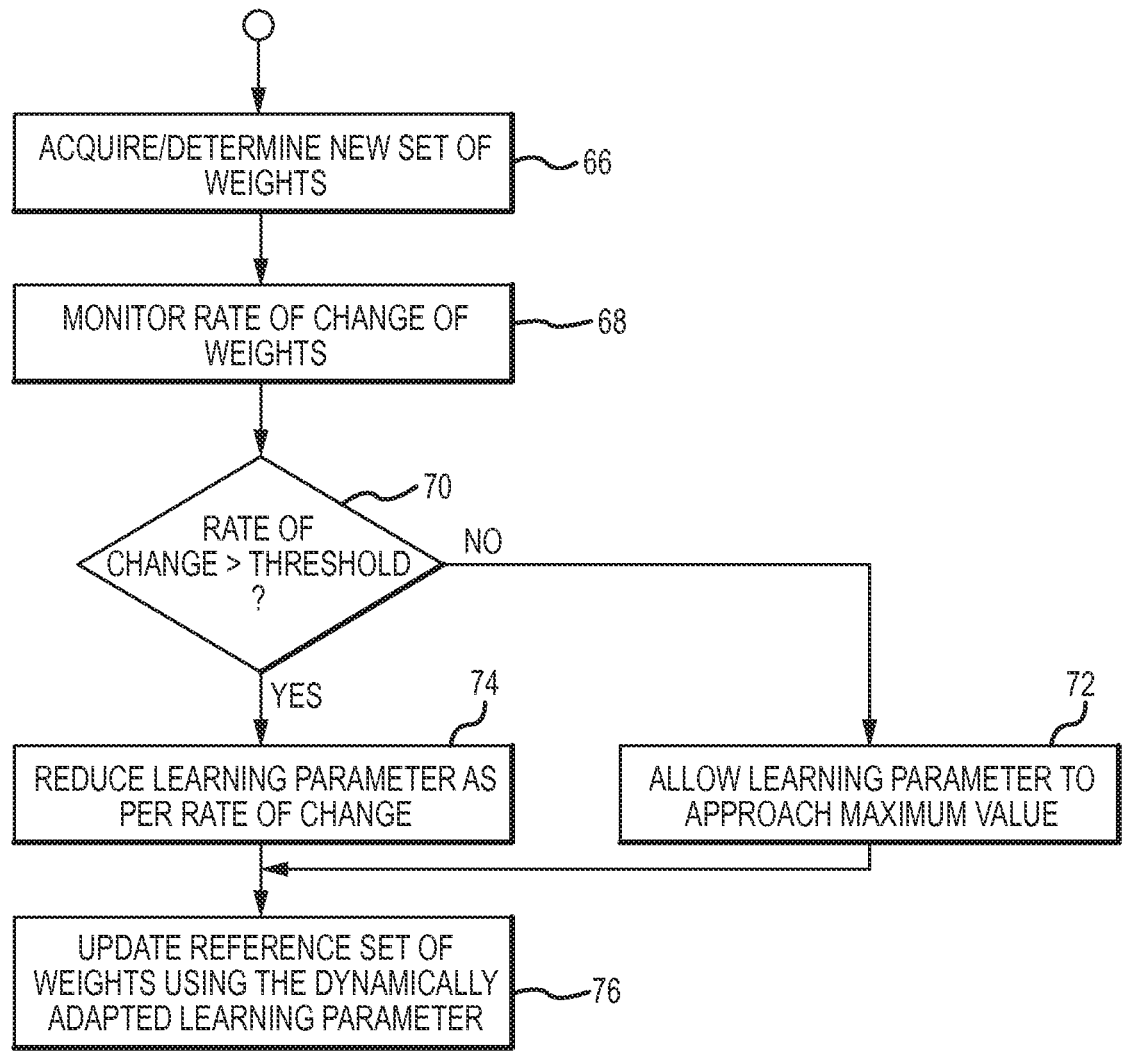
FIG. 9 is a flowchart diagram showing, in greater detail, a step of updating a reference set of weights shown in FIG. 8, which includes learning parameter λ dynamic adaptation.

FIG. 9 is a flowchart diagram showing, in greater detail, the step of updating weights, including dynamic adaptation of the learning parameter λ. The method begins in step 66.

In step 66, the method first involves acquiring a new set of weights. The step may be performed substantially as described above, based on newly collected patch impedance data and electrode location data and, for example, as set forth in equation (9) and the accompanying description. The method then proceeds to step 68.

In step 68, the method involves monitoring a rate of change of the weights between successively acquired sets of weights. This step may be performed by evaluating a distance, in a functional space, as described above in connection with equation (13) and the accompanying text. The method proceeds to step 70.

In step 70, the method determines whether the rate of change (i.e., the change in "distance" between successive weights) exceeds a threshold. This evaluation may be performed, in an embodiment, as set forth above in connection with equation (13). It should be understood that variations are possible. If the answer in this step is "NO," then the method branches to step 72, wherein the method allows the learning parameter to approach a predetermined maximum value, which in turn allows for rapid adaptation to new weights. On the other hand, if the answer in step 70 is "YES," then the method branches to step 74, where the learning parameter is reduced so as to suppress adaptation. In one embodiment, the learning parameter is suppressed exponentially as a function of the distance between successively-acquired sets of weights. In either case, the method proceeds to step 76.

In step 76, the method involves updating a reference set of weights using the dynamically adapted learning parameter. Again, this step may be performed substantially as described above (e.g., Eq. (11)).

FIGS. 10-14 show a first example of the results using the dynamic adaptation method described above. FIG. 10-14 in particular illustrate the Z-axis coordinate, whose value is affected by respiration artifacts and also by the catheter being moved by a physician to different locations in the heart. The data is shown about 10 minutes after the first respiration compensation weights were computed.

FIG. 10 shows an uncompensated Z-axis coordinate (designated as trace 78a) of an ablation catheter electrode containing respiration motion artifacts as the catheter is moved to different locations within the heart. FIG. 10 shows three distinct intervals. A first interval, designated as interval 80, corresponds to the catheter being positioned in an initial, first location within the heart. A second interval, designated interval 82, corresponds to the catheter being positioned in a second location within the heart. Finally, a third interval, designated interval 84, corresponds to the catheter being positioned in a third location within the heart. The trace 82 contains readily discernible respiration artifacts, for example, as encircled in region 86 during the second interval 82 and as encircled in region 88 during the third interval 84. No compensation has been applied to the data for trace 78a.

FIG. 11 shows the same data plotted in FIG. 10 but with motion compensation applied, now designated as trace 78b. The compensation for FIG. 11 does not employ dynamic adaptation. It should be appreciated that while the respiration artifacts are substantially missing in trace 78b when the catheter is in its initial location, residual respiration motion artifacts can still be seen after the catheter is moved to the second and third locations, as seen encircled in regions 86, 88.

FIG. 12 shows the results using motion compensation but with static 100% adaptation (i.e., where the learning parameter $\lambda=1$), plotted versus time and designated as trace 78c. The artifacts in the trace from using weights computed while the catheter was being moved are clearly seen (e.g., at points 90 and 92). These artifacts result from the coupling between the catheter movement and respiration signal on the patches (i.e., contained in the collected patch impedances).

FIG. 13 shows the results using motion compensation with static slow adaptation (i.e., where the learning parameter $\lambda=0.1$), plotted versus time and designated as trace 78d. While the slow adaptation shown in this Figure does not exhibit artifacts resulting from the intentional catheter movement, the adaptation is somewhat slow (e.g., with a settling time in excess of 50 seconds). Respiration motion artifacts can be seen encircled in region 94 during interval 84.

Figure 14:
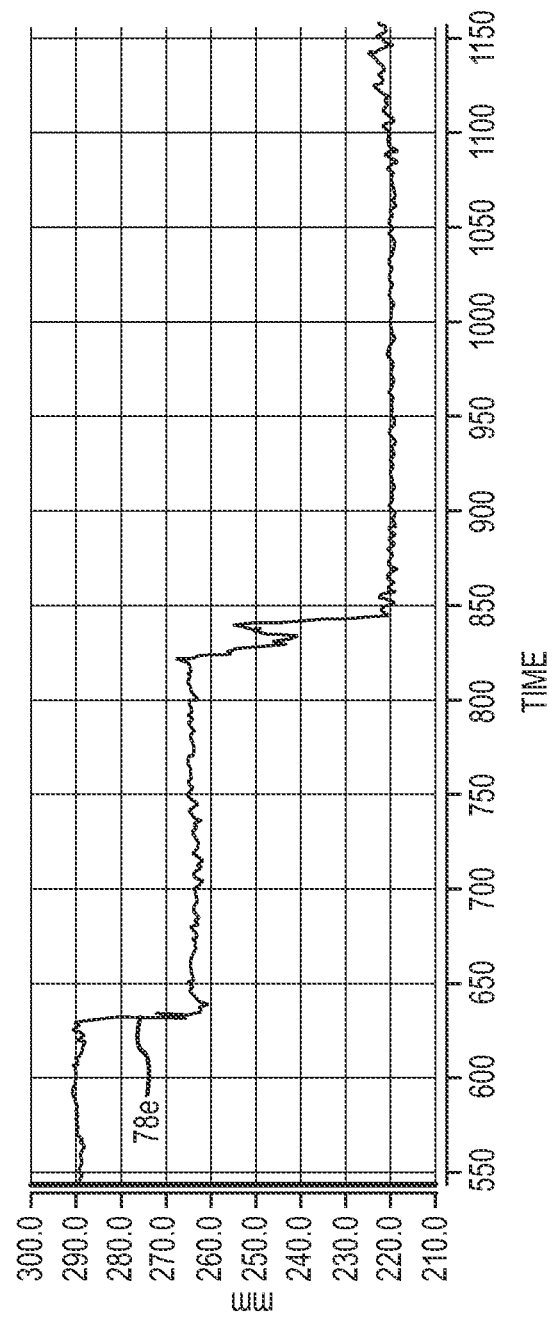
FIG. 14 shows the Z-coordinate component of FIG. 10 with applied compensation with dynamic adaptation.

FIG. 14 shows the results using motion compensation with dynamic adaptation where the acquired set of weights were updated at 3 second intervals and other parameters were set as follows: $\lambda_{max}=1$, $\gamma=2$. The adaptation time is reduced to below 15 seconds. Note, that the movement of the catheter to the third location (interval 84) in the heart does not exhibit the respiration artifacts as was seen in FIGS. 12-13.

Figure 15:
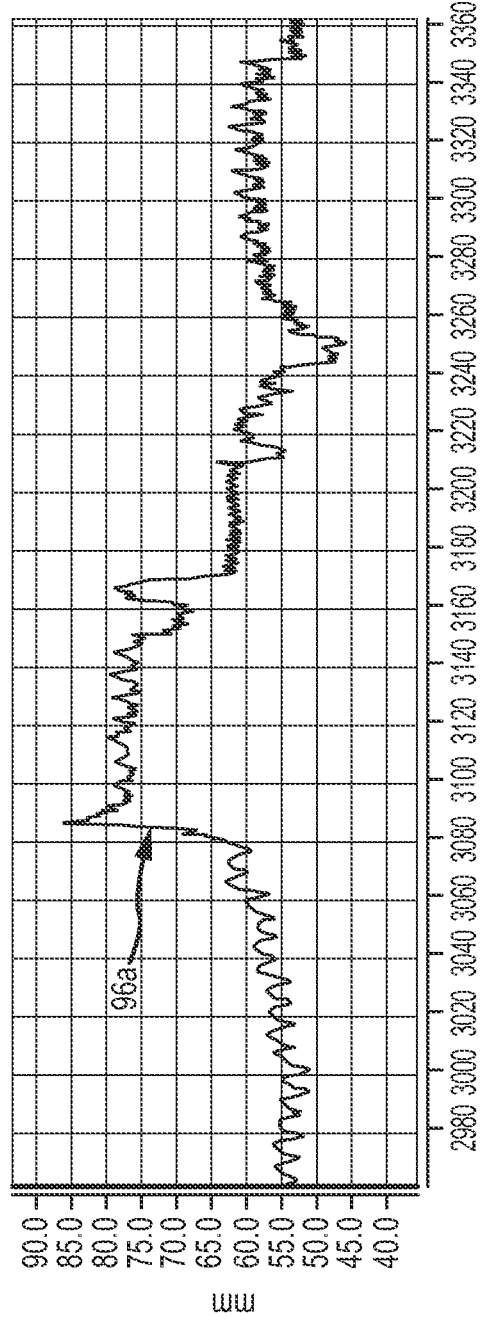
FIG. 15 shows an uncompensated catheter displacement versus time signal without any applied compensation.
Figure 16:
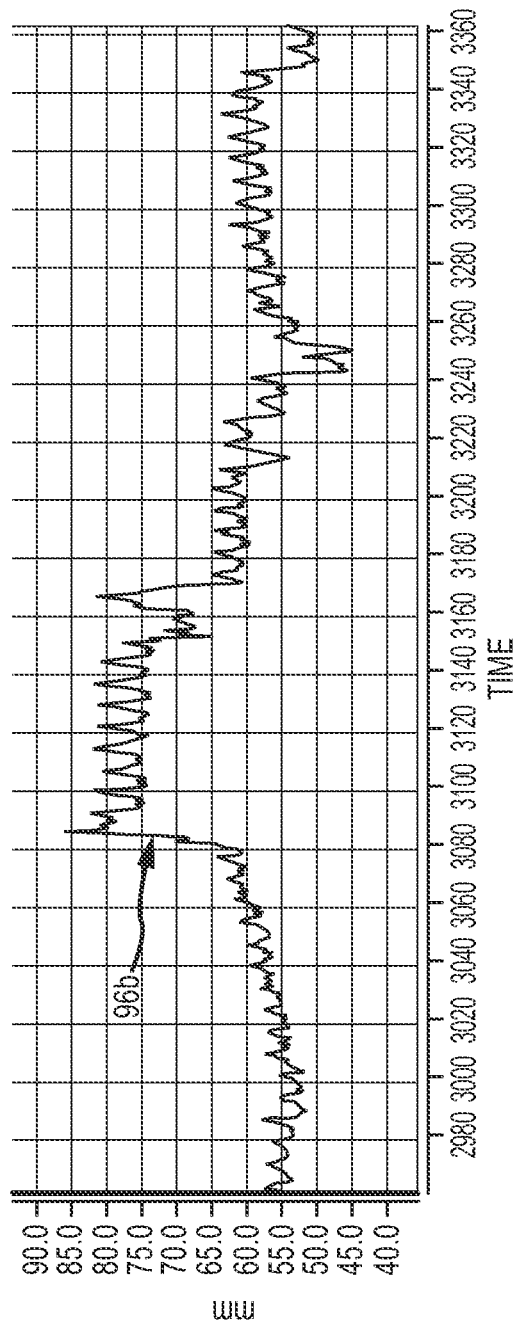
FIG. 16 shows the catheter displacement signal of FIG. 15 with applied compensation but with no adaptation wherein use of hour-old weights results in an amplified respiration artifact.
Figure 17:
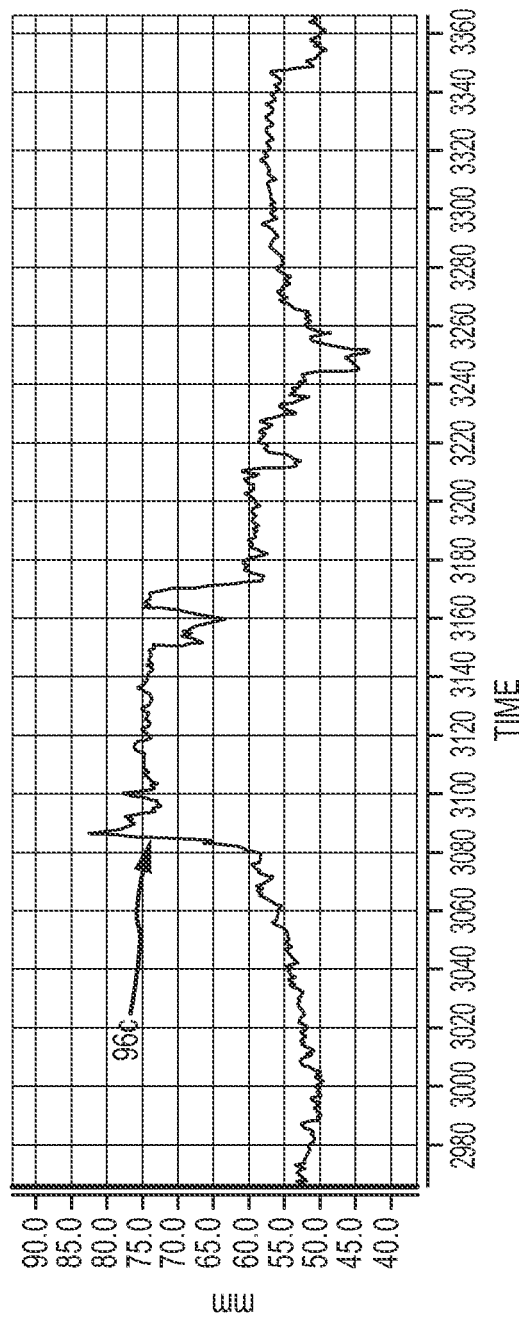
FIG. 17 shows the catheter displacement signal of FIG. 15 with applied compensation and with dynamic adaptation.

FIGS. 15-17 show another example where the catheter was displaced from its original position, which is plotted versus time. In addition, the data is shown about 1 hour after the original set of weights was computed.

FIG. 15 is a catheter (i.e., electrode thereof) displacement versus time diagram. The displacement over time is designated as trace 96a. No respiration compensation was applied. Accordingly, the respiration artifacts may be clearly seen imposed on the trace 96a.

FIG. 16 shows the catheter displacement versus time, designated trace 96b, and reflects respiration compensation with no adaptation. However, the compensation applied was based data acquired (and weights computed) about one hour previous. The respiration artifacts contained in trace 96b are actually amplified relative to the artifacts in trace 96a by using hour-old weights. Thus, FIG. 16 demonstrates that if the set of weights are not updated (i.e., through learning parameter adaptation), the use of such compensation may actually result in amplification of the very artifacts the method seeks to nullify.

FIG. 17 shows the catheter displacement versus time, designated trace 96c, and reflects respiration compensation with dynamic adaptation (as described above). FIG. 17 demonstrates the effectiveness of compensation with dynamic adaptation in cancelling the undesired artifacts (i.e., respiration, cardiac).

Automatic Gain Control.

The automatic compensation gain control block 36 (FIG. 1) is configured to selectively suppress compensation when certain conditions are detected. In an embodiment, the gain control block 36 may be configured to perform the functionality described below, including the description of steps through equations (14) through (16) below. Note that various embodiments described herein for compensating for respiration/cardiac artifacts involves the use of both electrode location and patch impedance data (i.e., see Equation (10)). Every time one combines electrode and patch impedance data there is a potential to reduce the accuracy of the positional measurements due to the noise and irregularities introduced by the patch impedances themselves. For example, some patches may be noisier than catheter electrodes, and susceptible to variability as well. Use of such information may manifest itself in significant visible transient displacement of the electrode's location, e.g., on a screen display. To counter this undesired behavior, certain embodiments of the invention are configured to incorporate automatic compensation gain control. In other embodiments, gain control is used in combination with the dynamic adaptation feature described above. Automatic compensation gain control will now be described.

First, the expression for the compensated signal (Eq. (10)) is adjusted according to the following equation (14):

$$X_i^{jcorrected} = X_i - g \sum_{j=0}^{M} \tilde{P}_i^j \cdot W^j, \quad (14)$$

where a new gain parameter g is defined and where 0≤g≤1. The value of g is determined based on the following considerations. By default, the gain is set to a value of one (1). The gain remains set to 1 unless the logic described below determines that the gain parameter should be reduced.

Second, conditions are assessed to determine whether the default value for g should be altered. Recall that the respiration compensation is that portion of equation (10) that is subtracted from the uncompensated electrode location. The respiration compensation is isolated and reproduced in Eq. (15) below.

$$resp\_corr_i = \sum_{j=0}^{M} \tilde{P}_i^j \cdot W^j \quad (15)$$

Note that the respiration compensation is computed in a substantially continuous manner. Determining whether the gain parameter's default should be reduced involves computing the respiration correction's exponential moving average (mean) and its average deviation therefrom, referred to herein as mean_resp_deviation over a predetermined time period (e.g., a time constant of 30 seconds in one embodiment). The next step involves determining the absolute value of the deviation of the current correction value (i.e., of the compensation signal) from the moving average, which will be referred to as the current_deviation. When the current_deviation exceeds a threshold (e.g., 10 times the standard deviation), the logic reduces the gain parameter g according to the following empirical formulae set forth in Eq. (16):

$$g = 2 \cdot \frac{\text{mean\_resp\_deviation}}{\text{current\_deviation}} \quad (16)$$

In an embodiment, the deviations are computed as lengths of 3-dimensional vectors. The exponential moving average and average deviation are used in an embodiment in order to make the computation efficient and reduce memory requirements as compared to more formal computed moving averages and standard deviations. Variations are possible.

FIGS. 18A-B and FIGS. 19-20 illustrate various X, Y and Z-axis plots versus time of electrode location and patch impedance data, showing the positive effect of the gain control feature described above.

Figure 18A:
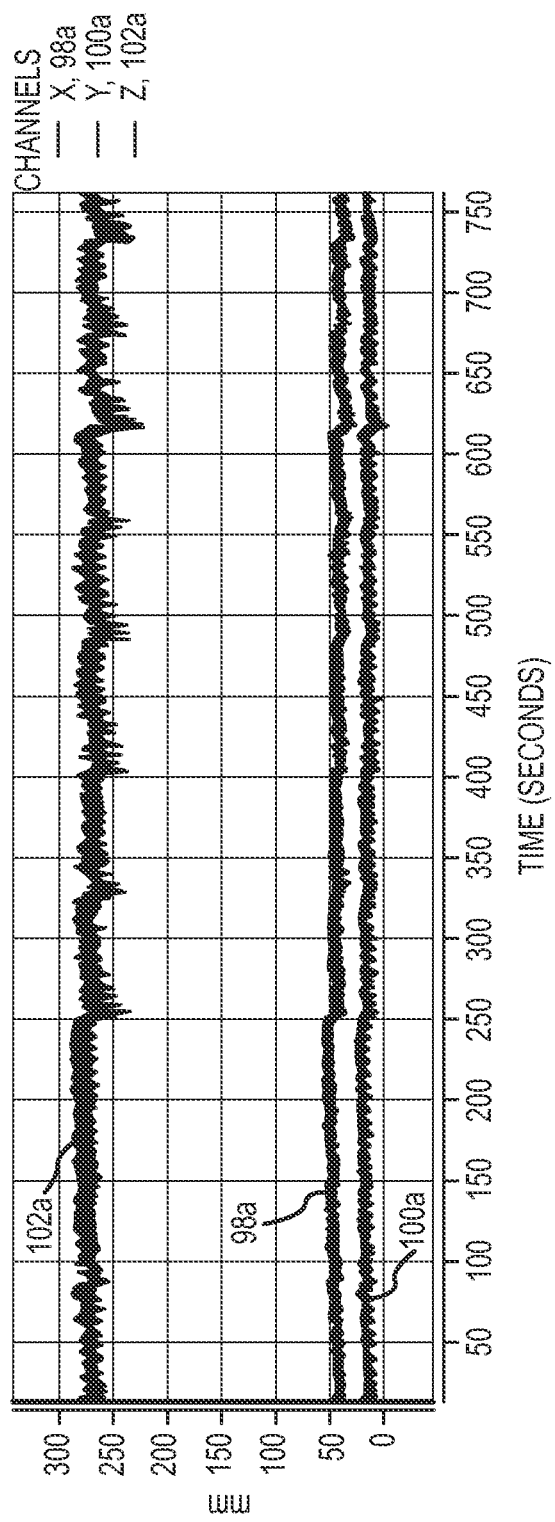
FIGS. 18A-18B show uncompensated plots of X, Y and Z-coordinate components versus time and a corresponding bio-impedance signal, showing spikes during certain phases of the respiration cycle.
Figure 18B:
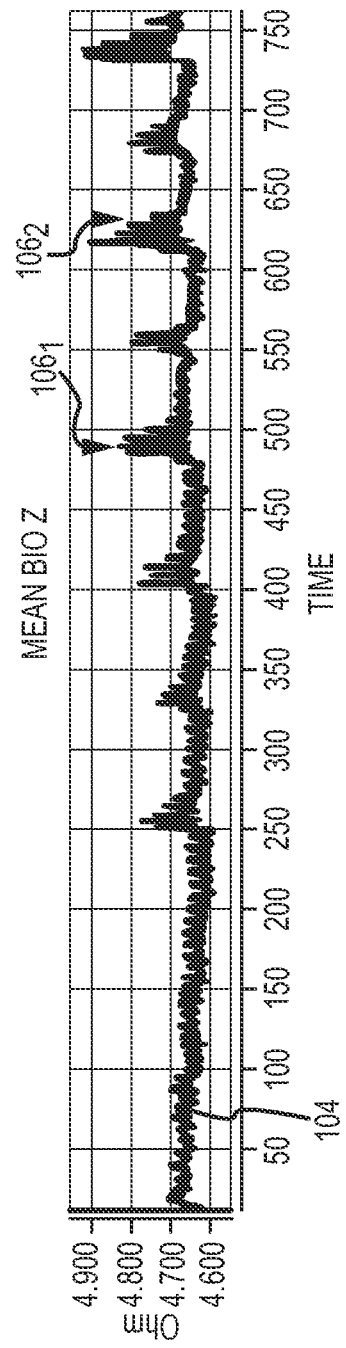

FIG. 18A, in particular, is a displacement versus time diagram showing, separately, X, Y, and Z-axis coordinates (traces 98a, 100a and 102a, respectively) of a catheter electrode. FIG. 18B is an impedance versus time diagram showing a mean bio-impedance, designated as trace 104. The mean bio-impedance is provided to represent an overall reflection of the patch impedances.

FIGS. 18A-18B are aligned to the same time-line to facilitate comparison of the various traces. The respiratory and cardiac components are seen in all of the traces 98a, 100a, 102a and 104. Note that the bio-impedance trace 104 contains sharp spikes, for example, at points $106_1$ and $106_2$, due to the increased cardiac amplitude during certain phases of the respiration cycle.

FIG. 19 shows the X, Y and Z-axis coordinates again plotted versus time with respiration compensation but without compensation gain control. The updated coordinates are now respectively designated as traces 98b, 100b and 102b. Application of respiration compensation without automatic gain control results in the appearance of sharp spikes in the electrode positions (e.g., at times t=250 seconds and t=730 seconds). The spikes have amplitudes in excess of 100 mm, which will be seen on a display screen as very large transient shifts (i.e., very objectionable), and which may result in the catheter literally moving outside of the visible area of the screen during an electrophysiological procedure.

FIG. 20 shows the X, Y and Z-axis coordinates again plotted versus time with respiration compensation but now also with compensation gain control. The updated coordinates are respectively designated as traces 98c, 100c and 102c. The compensation gain control feature as described above eliminates the spikes that were evident in FIG. 19.

In another embodiment, the motion compensation approach described herein, including dynamic adaptation, may be used in a hybrid positioning system that includes the above-described impedance-based positioning system as a first positioning sub-system and a magnetic field based position system as a second positioning sub-system. The magnetic field based positioning sub-system (not shown) may comprise magnetic field transmitter(s) and a magnetic field sensor (e.g., coil sensor) located on or within a medical device such as a catheter, as seen, for example only, by reference to U.S. Pat. No. 6,233,476, hereby incorporated by reference in its entirety. The compensation approach described herein, as applied to the hybrid positioning system, can be used to compensate position coordinates obtained from the magnetic field based positioning sub-subsystem (hereinafter "magnetic coordinates") for motion artifacts (e.g., respiration and cardiac motion, as described above) as well as other distortions (e.g., if a metal object is introduced into the magnetic field established by the magnetic positioning sub-system, thus distorting the magnetic field, the compensation approach adapts automatically to generate an appropriate respiration compensation signal).

In the hybrid embodiment, the body surface electrode ("patch") signals described above can be used as references for the magnetic field based positioning sub-system. The motion artifacts (e.g., respiration and/or cardiac) contained in the magnetic coordinates can be removed in exactly the same way as described above. For example, in FIG. 1, localization block 32 may be modified to provide magnetic coordinates, with the remainder of FIG. 1 remaining the same. Thus, the magnetic coordinates associated with a magnetic field sensor (i.e., in substitution of the catheter electrode coordinates) are provided by the modified localization block 32, and the methods as described above apply in the same way. Thus, the motion compensation block 34 producing compensation signal 35, automatic compensation gain control block 36 and combination mechanism 37 as shown in FIG. 1 may remain the same and operate the same. Thus, the signals from the patches are used and processed in the same way as described above for computing the compensation signal. Moreover, the dynamic adaptation described above is also applicable, and adapts (automatically) the compensation methodology to generate an appropriate respiration compensation signal. In sum, the hybrid system operates the same as described above, except that coordinates obtained from the magnetic sub-system are being compensated rather than the coordinates from the impedance-based positioning subsystem.

It should be understood that a medical device contemplated here may include a magnetic field positioning sensor and one or more electrodes that can be used for impedance-based position determination. That being said, in further embodiments, medical devices with just one or more magnetic field sensor(s) may be used and for which the magnetic coordinates determined from signals obtained therefrom may be compensated by using the patch impedance signals and methodology described above.

It should be appreciated that the dynamic adaptation feature described herein is effective in maintaining accurate motion compensation of respiration and cardiac artifacts, even with changing respiration patterns or movement of the catheter to different locations in the body. In addition, the automatic gain control feature is effective in suppressing undesired effects that would otherwise be introduced by patch noise/interference and/or sudden changes in patch impedance.

It should be understood that variations of the compensation approaches described herein are possible. For example, in a further embodiment, a location-specific compensation scheme is provided. In this further embodiment, the system, using one electrode, computes the compensation at a specific location in the body of the patient (e.g., as defined by the location of the one electrode in a reference coordinate system) and then applies that compensation to other electrodes when such other electrodes are moved into the vicinity of the specific location. Such "other" electrodes may include the same electrode that was used in computing the compensation but taken at a later point in time. The compensation block may be thus configured to associate the compensation determined at a specific location with its corresponding coordinate within the reference coordinate system, to yield a compensation-coordinate data pair. This associating step is repeated for a plurality of electrode locations and resulting data pairs may be recorded in a data structure such as a compensation database. Alternatively, each computed compensation may be associated with a region (e.g., a volume of a predetermined size) surrounding a specific location. The compensation block, in either case, is configured to refer to the compensation database to retrieve an appropriate correction/compensation for the "other" electrode, based on the specific location of the "other" electrode (e.g., using the specific electrode location as an index into the compensation database).

It should be understood that the system 20 as described above may include conventional processing apparatus known in the art, capable of executing pre-programmed instructions stored in an associated memory, all performing in accordance with the functionality described herein. It is contemplated that the methods described herein will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for determining a motion compensated location of an electrode of a medical device within a body of a patient, comprising:
   a computer system including (i) a localization block configured to produce an uncompensated electrode location; (ii) a motion compensation block configured to generate a compensation signal, said computer system being configured to subtract said compensation signal from said uncompensated electrode location to output a motion compensated electrode location;
   said motion compensation block being configured to: (i) mean-adjust patch electrode impedance data associated with body surface electrodes and to mean-adjust electrode location data associated with said electrode; (ii) acquire a set of weights by equating the product of said set of weights and said mean-adjusted patch impedance data with said mean-adjusted electrode location data; (iii) further mean-adjust patch impedance and electrode location data for further time periods to produce a plurality of successive acquired sets of weights; (iv) for each successive acquired sets of weights update a reference set of weights, based on a learning parameter, wherein said learning parameter is determined in accordance with a distance between the successive acquired sets of weights; and (v) generate said compensation signal based on said updated reference set of weights and patch electrode impedance data.

2. An apparatus for determining a motion compensated location of an electrode of a medical device within a body of a patient, comprising:
   a computer system including (i) a localization block configured to produce an uncompensated electrode location; (ii) a motion compensation block configured to generate a compensation signal, said computer system being configured to subtract said compensation signal from said uncompensated electrode location to output a motion compensated electrode location;
   said motion compensation block being configured to: (i) mean-adjust patch electrode impedance data associated with body surface electrodes and to mean-adjust electrode location data associated with said electrode; (ii) acquire a set of weights such that a linear combination of the product of said set of weights and said mean-adjusted patch impedance data correspond to said mean-adjusted electrode location data; (iii) further mean-adjust patch impedance and electrode location data for further time periods to produce a plurality of successive acquired sets of weights; (iv) for each successive acquired sets of weights update a reference set of weights, based on a learning parameter, wherein said learning parameter is determined in accordance with a distance between the successive acquired sets of weights; and (v) generate said compensation signal based on said updated reference set of weights and patch electrode impedance data.

3. The apparatus of claim 2 wherein said mean-adjusted patch electrode impedance data and said mean-adjusted electrode location data are in matrix form, said motion compensation block being further configured (i) to perform singular value decomposition of the mean-adjusted patch electrode impedance data; (ii) to obtain the pseudo-inverse of said mean-adjusted patch electrode impedance data matrix and to apply regularization; and (iii) to determine said acquired set of weights in accordance with the product of said pseudo-inverse mean-adjusted patch electrode impedance data matrix and said mean-adjusted electrode location data matrix.

4. The apparatus of claim 2 wherein said motion compensation block is further configured to sum said reference set of weights with the product of said learning parameter and a difference between a most-recently acquired set of weights and said reference set of weights.

5. The apparatus of claim 4 wherein said motion compensation block is further configured to vary said learning parameter in accordance with a distance between successive, acquired sets of weights.

6. The apparatus of claim 2 wherein said motion compensation block is further configured to compute said compensation signal as a function of a gain parameter.

7. The apparatus of claim 6 wherein said motion compensation block is further configured to determine (i) a moving average of said compensation signal; (ii) an average deviation of said compensation signal from said moving average; and (iii) a value of said gain parameter as a function of a ratio of said average deviation and a current deviation between the current compensation signal and said moving average.

8. The apparatus of claim 2 wherein said electrode is a first electrode and said motion compensated electrode location is a compensated first electrode location having associated therewith a coordinate within a reference coordinate system, said localization block being configured to determine an uncompensated second electrode location associated with a second electrode, said motion compensation block being further configured to apply said compensation signal to said uncompensated second electrode location to produce a motion compensated second electrode location when said uncompensated second electrode location matches said coordinate within a predetermined range.

9. The apparatus of claim 2 wherein said uncompensated electrode location includes one of a position and orientation (P&O) in a reference coordinate system, wherein said motion compensation block is further configured to acquire a respective set of weights for each selected axis in the reference coordinate system.

10. The apparatus of claim 2 wherein said motion compensation block is further configured to acquire said set of weights involving principal component analysis (PCA).

11. The apparatus of claim 2 wherein said motion compensation block is configured to exponentially reduce the learning parameter when the distance between successive, acquired sets of weights exceeds a threshold to thereby suppress learning parameter adaptation.

12. The apparatus of claim 2 wherein said motion compensation block is further configured to acquire (i) said patch electrode impedance data using associated body surface electrodes and (ii) said uncompensated electrode location data using said electrode of said medical device.

13. The apparatus of claim 2 wherein said computer system main control unit is configured to generate a visual representation of the medical device on a display based on the motion compensated electrode location.

14. The apparatus of claim 2 wherein said compensation signal corresponds to motion artifacts associated with said uncompensated electrode location and wherein said motion compensation signal is configured to reduce such motion artifacts associated with said uncompensated electrode location.

15. The apparatus of claim 14 wherein said motion artifacts comprise at least one of respiration-induced motion artifacts and cardiac motion artifacts.

* * * * *